US012678102B2

(12) United States Patent
Xu et al.

(10) Patent No.: US 12,678,102 B2
(45) Date of Patent: Jul. 14, 2026

(54) METHOD OF MEASURING TISSUE ELEMENT, DEVICE OF MEASURING TISSUE ELEMENT, AND WEARABLE APPARATUS

(71) Applicant: SUNRISE TECHNOLOGIES CO., LTD., Beijing (CN)

(72) Inventors: Kexin Xu, Beijing (CN); Tongshuai Han, Beijing (CN); Picheng Zhao, Beijing (CN); Mingfei Yao, Beijing (CN)

(73) Assignee: SUNRISE TECHNOLOGIES CO., LTD., Beijing (CN)

( * ) Notice: Subject to any disclaimer, the term of this patent is extended or adjusted under 35 U.S.C. 154(b) by 370 days.

(21) Appl. No.: 18/264,617

(22) PCT Filed: Dec. 31, 2021

(86) PCT No.: PCT/CN2021/143512
§ 371 (c)(1),
(2) Date: Aug. 8, 2023

(87) PCT Pub. No.: WO2022/170882
PCT Pub. Date: Aug. 18, 2022

(65) Prior Publication Data
US 2024/0115204 A1 Apr. 11, 2024

(30) Foreign Application Priority Data
Feb. 11, 2021 (CN) .......................... 202110185766.1

(51) Int. Cl.
*A61B 5/1455* (2006.01)
*A61B 5/00* (2006.01)

(52) U.S. Cl.
CPC .......... *A61B 5/6843* (2013.01); *A61B 5/1455* (2013.01); *A61B 5/6802* (2013.01)

(58) Field of Classification Search
CPC .............. A61B 5/1455; A61B 5/14551; A61B 5/14552; A61B 5/683
See application file for complete search history.

(56) References Cited

U.S. PATENT DOCUMENTS 4,859,057 A * 8/1989 Taylor ................ A61B 5/14551
600/323
5,158,090 A 10/1992 Waldman et al.
(Continued)

FOREIGN PATENT DOCUMENTS

CN 1032587 A 4/1989
CN 101002683 A 7/2007
(Continued)

OTHER PUBLICATIONS

Extended European Search Report for European Application No. 21925527.0 dated Dec. 16, 2024, 11 pages.
(Continued)

*Primary Examiner* — Eric F Winakur
(74) *Attorney, Agent, or Firm* — Westman, Champlin & Koehler, P.A.

(57) ABSTRACT

A method of measuring a tissue element, a device of measuring a tissue element, and a wearable apparatus are provided. The method includes: irradiating a measurement region with incident light having at least one predetermined wavelength (S110), where each beam of the incident light is incident on an incident position to form at least one beam of exit light exited from at least one exit position on the measurement region; and arranging an anti-jitter portion at a position corresponding to the measurement region, so that an average optical path of exit light received by a measurement probe associated with the anti-jitter portion is maintained within a predetermined optical path range during a skin jitter process at the measurement region (S120).

17 Claims, 14 Drawing Sheets

Movement direction of anti-jitter portion
Movement direction of anti-jitter portion
Incident position D
Incident light
Incident light
Incident position D
Exit light
Exit light
Exit position E
Exit light
Exit position E
Vessel state 1
Direction of skin jitter
Direction of skin jitter

(56) References Cited

U.S. PATENT DOCUMENTS

| | | | | |
|---|---|---|---|---|
| 5,224,478 | A * | 7/1993 | Sakai | A61B 5/14552 |
| | | | | 600/335 |
| 5,676,142 | A | 10/1997 | Miwa et al. | |
| 6,104,946 | A | 8/2000 | Tsuchiya et al. | |
| 6,839,585 | B2 * | 1/2005 | Lowery | A61B 5/14552 |
| | | | | 600/344 |
| 7,299,080 | B2 | 11/2007 | Acosta et al. | |
| 8,346,329 | B2 | 1/2013 | Xu et al. | |
| 8,700,116 | B2 * | 4/2014 | Schlottau | A61B 5/14551 |
| | | | | 600/323 |
| 10,575,766 | B2 | 3/2020 | Sato | |
| 11,204,315 | B2 | 12/2021 | Luo et al. | |
| 2002/0058864 | A1 | 5/2002 | Mansfield et al. | |
| 2005/0020892 | A1 | 1/2005 | Acosta et al. | |
| 2005/0049466 | A1 | 3/2005 | Blank et al. | |
| 2005/0267341 | A1 | 12/2005 | Blank et al. | |
| 2006/0118742 | A1 | 6/2006 | Levenson et al. | |
| 2007/0219437 | A1 | 9/2007 | Schurman et al. | |
| 2008/0171925 | A1 | 7/2008 | Xu et al. | |
| 2012/0101347 | A1 | 4/2012 | Amano et al. | |
| 2014/0343383 | A1 | 11/2014 | Sato | |
| 2016/0018327 | A1 | 1/2016 | Hogan | |
| 2016/0242682 | A1 | 8/2016 | Gulati et al. | |
| 2016/0249836 | A1 | 9/2016 | Gulati et al. | |
| 2017/0164878 | A1 | 6/2017 | Connor | |
| 2018/0168496 | A1 | 6/2018 | Sato | |
| 2019/0133469 | A1 | 5/2019 | Just et al. | |
| 2020/0240905 | A1 | 7/2020 | Luo et al. | |
| 2020/0345418 | A1 | 11/2020 | Varghese et al. | |
| 2020/0405188 | A1 | 12/2020 | Sharma et al. | |
| 2022/0054051 | A1 | 2/2022 | Xu et al. | |

FOREIGN PATENT DOCUMENTS

| | | | |
|---|---|---|---|
| CN | 106132299 | A | 11/2016 |
| CN | 107144555 | A | 9/2017 |
| CN | 107242855 | A | 10/2017 |
| CN | 108309244 | A | 7/2018 |
| CN | 109738358 | A | 5/2019 |
| CN | 109984725 | A | 7/2019 |
| CN | 111317442 | A | 6/2020 |
| CN | 111317443 | A | 6/2020 |
| EP | 0834277 | A1 | 4/1998 |
| JP | H05503856 | A | 6/1993 |
| JP | 2007532183 | A | 11/2007 |
| JP | 2010148685 | A | 7/2010 |
| JP | 2011110085 | A | 6/2011 |
| JP | 2014042579 | A | 3/2014 |
| JP | 2016010717 | A | 1/2016 |
| KR | 1020160047964 | A | 5/2016 |
| WO | 2015066224 | A2 | 5/2015 |
| WO | 2020119825 | A | 6/2020 |

OTHER PUBLICATIONS

Translation of Notice of Preliminary Rejection for Korean Application No. 10-2023-7030775, dated Jul. 4, 2025, 18 pages.

Translation of Notice of Preliminary Rejection for corresponding Korean Application No. 10-2023-7030775, dated Apr. 15, 2025, 24 pages.

Translation of Notification of Reasons for Refusal for Japanese Application No. 2023548694, dated Feb. 17, 2025, 8 pages.

International Search Report and Written Opinion from International Application No. PCT/CN2021/143512, dated Mar. 29, 2022.

First Office Action, including Search Report, for Chinese Patent Application No. 202110185766.1, dated Aug. 2, 2022, 23 pages.

Notice of Reasons for Refusal, for corresponding Japanese Patent Application No. 2023-548694, dated Aug. 13, 2024, 6 pages.

Translation of Japanese Office Action for Japanese Patent Application No. JP 2023548694, dated Oct. 24, 2025, 4 pages.

Translation of Korean Office Action for Korean Application No. 10-2023-7030775, dated Sep. 30, 2025, 22 pages.

Kirilina et al. "Identifying and quantifying main components of physiological noise in functional near infrared spectroscopy on the prefrontal cortex," Frontiers in Human Neuroscience vol. 7, 17 pages, 2013.

European Office Action for European Application No. 21925527.0 dated Apr. 14, 2026, 8 pages.

* cited by examiner

S110

A measurement region is irradiated with incident light having at least one predetermined wavelength

S120

An anti-jitter portion is arranged at a position corresponding to the measurement region, so that an average optical path of exit light received by a measurement probe associated with the anti-jitter portion is maintained within a predetermined optical path range during a skin jitter process at the measurement region

FIG. 1

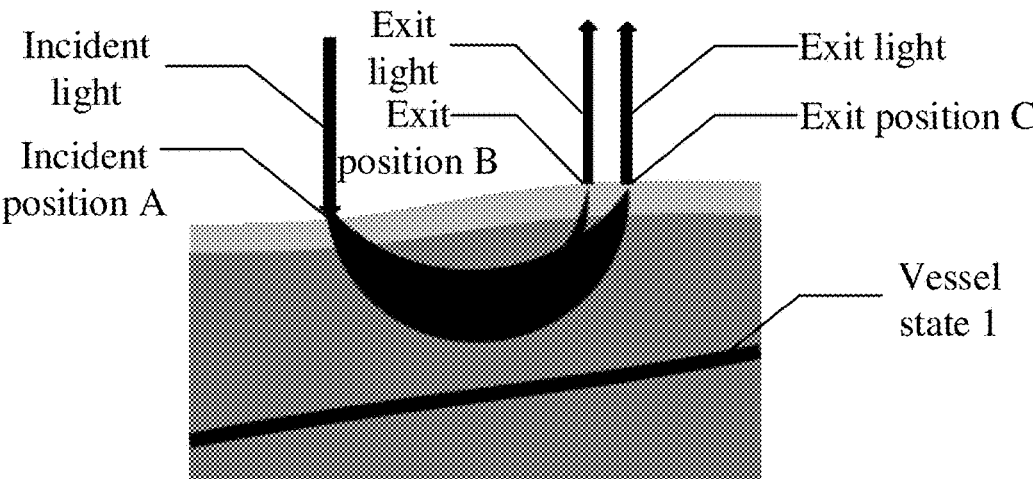

FIG. 2

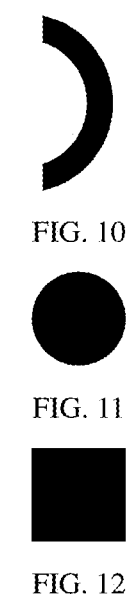
FIG. 10
FIG. 11
FIG. 12
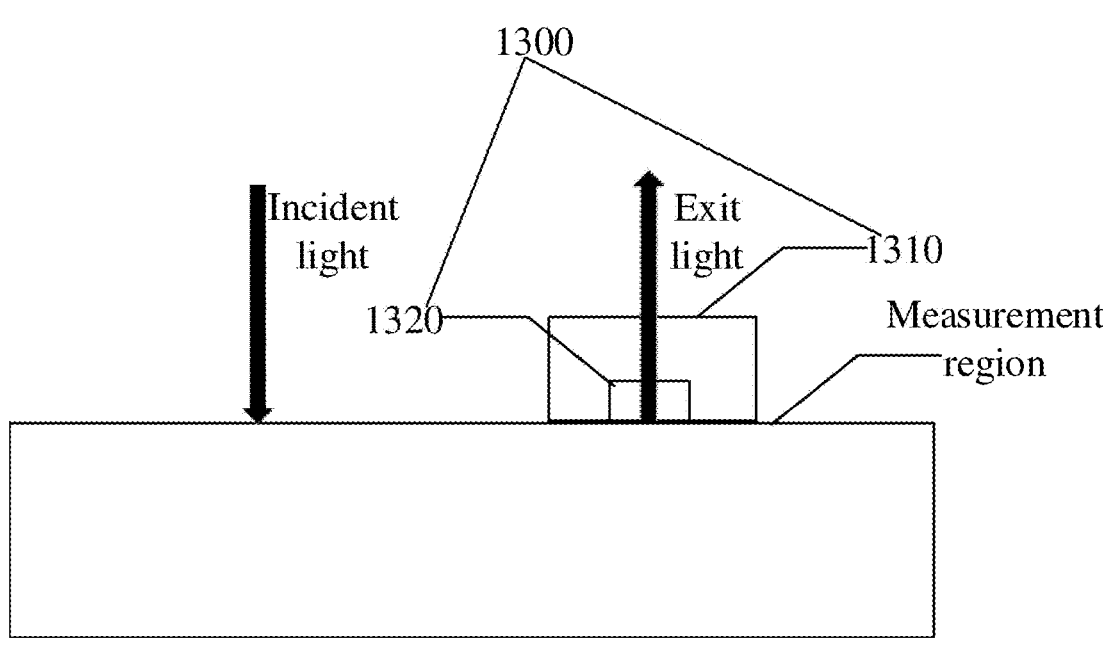
FIG. 13

3200

METHOD OF MEASURING TISSUE ELEMENT, DEVICE OF MEASURING TISSUE ELEMENT, AND WEARABLE APPARATUS

CROSS-REFERENCE TO RELATED APPLICATION(S)

This application is a Section 371 National Stage Application of International Application No. PCT/CN2021/143512, filed on Dec. 31, 2021, entitled "METHOD OF SUPPRESSING INFLUENCE OF JITTER, DEVICE OF SUPPRESSING INFLUENCE OF JITTER, AND WEARABLE APPARATUS", which published as WIPO Publication No. WO 2022/170882 A1, on Aug. 18, 2022, which claims priority to Chinese Application No. 202110185766.1, filed on Feb. 11, 2021, the contents of which are hereby incorporated by reference in their entireties.

TECHNICAL FIELD

Embodiments of the present disclosure relate to a field of spectrum detection technology, and in particular, to a method of measuring a tissue element, a device of measuring a tissue element, and a wearable apparatus.

BACKGROUND

A variety of tissue elements, such as blood glucose, fat, and white blood cells, etc. are contained in a body fluid of a human body. A concentration of each tissue element is required to be within a corresponding concentration range to ensure a healthy operation of the human body. However, for some individuals, the tissue element is prone to imbalance, that is, the concentration of the tissue element is not within a numerical range, which may lead to diseases, and endanger health and even life. For such objects, there is a need to perform a real-time measurement on the tissue element.

An optical method has characteristics of rapidness, non-invasiveness, and multidimensional information, etc., and is generally adopted to measure a tissue element in a related art. According to a measurement principle, the optical method mainly includes Raman spectrometry, polarization method, optical coherence tomography method, photo-acoustic spectrometry, mid-infrared spectrometry and near-infrared spectrometry.

In a process of implementing concepts of the present disclosure, the inventors found that the related art has at least a problem that a measurement accuracy is not high in the related art.

SUMMARY

In view of this, embodiments of the present disclosure provide a method of measuring a tissue element, a device of measuring a tissue element, and a wearable apparatus.

In an aspect of embodiments of the present disclosure, a method of measuring a tissue element is provided, including: irradiating a measurement region with incident light having at least one predetermined wavelength, where each beam of the incident light is incident on an incident position to form at least one beam of exit light exited from at least one exit position on the measurement region; and arranging an anti-jitter portion at a position corresponding to the measurement region, so that an average optical path of exit light received by a measurement probe associated with the anti-jitter portion is maintained within a predetermined optical path range during a skin jitter process at the measurement region. The method further includes: after arranging the anti-jitter portion at the position corresponding to the measurement region, obtaining an output light intensity corresponding to each beam of the exit light acquired by the measurement probe; and determining a concentration of a measured tissue element according to at least one output light intensity corresponding to the at least one predetermined wavelength.

In another aspect of embodiments of the present disclosure, a device of measuring a tissue element is provided, including: an anti-jitter portion arranged at a position corresponding to a measurement region, so that an average optical path of exit light received by a measurement probe associated with the anti-jitter portion is maintained within a predetermined optical path range during a skin jitter process at the measurement region, where the exit light is obtained by irradiating the measurement region with incident light having at least one predetermined wavelength, and each beam of the exit light is formed by incident light incident on an incident position and exited from an exit position on the measurement region; an obtaining module configured to obtain an output light intensity corresponding to each beam of the exit light acquired by the measurement probe; and a processing module configured to determine a concentration of a measured tissue element according to at least one output light intensity corresponding to the at least one predetermined wavelength.

In another aspect of embodiments of the present disclosure, a wearable apparatus is provided, including the device of measuring a tissue element as described above.

BRIEF DESCRIPTION OF THE DRAWINGS

The above and other objectives, features and advantages of the present disclosure will be clearer with following descriptions of embodiments of the present disclosure with reference to the accompanying drawings, in which:

FIG. 1 schematically shows a flowchart of a method of measuring a tissue element according to embodiments of the present disclosure;

FIG. 2 schematically shows a schematic diagram of a measurement probe receiving exit light when no anti-jitter portion is arranged at a position corresponding to a measurement region according to embodiments of the present disclosure;

FIG. 10 schematically shows a schematic diagram of a sector-ring photosensitive surface according to embodiments of the present disclosure;

FIG. 11 schematically shows a schematic diagram of a circular photosensitive surface according to embodiments of the present disclosure;

FIG. 12 schematically shows a schematic diagram of a square photosensitive surface according to embodiments of the present disclosure;

FIG. 13 schematically shows a schematic diagram of a device of measuring a tissue element according to embodiments of the present disclosure;

DETAILED DESCRIPTION OF EMBODIMENTS

Figure 3:
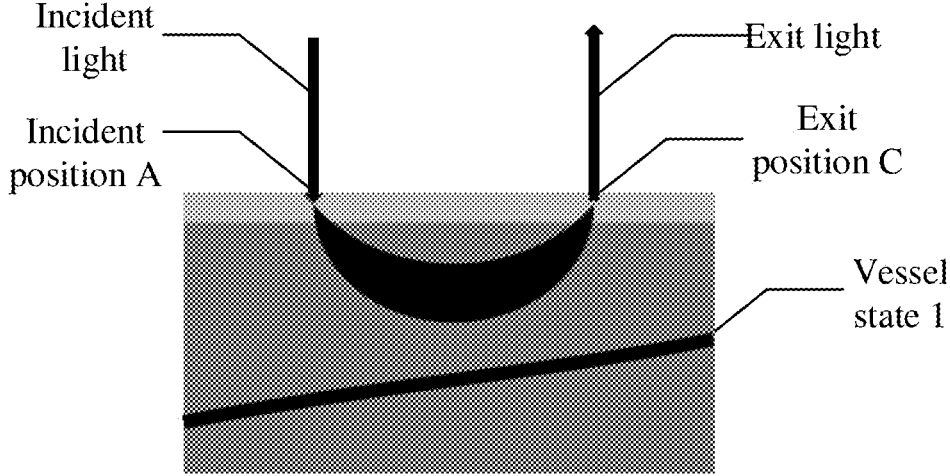
FIG. 3 schematically shows a schematic diagram of a measurement probe receiving exit light when an anti-jitter portion is arranged at a position corresponding to a measurement region according to embodiments of the present disclosure.

Embodiments of the present disclosure will be described below with reference to the accompanying drawings. It should be understood, however, that these descriptions are merely exemplary and are not intended to limit the scope of the present disclosure. In the following detailed descriptions, for ease of interpretation, many specific details are set forth to provide a comprehensive understanding of embodiments of the present disclosure. However, it is clear that one or more embodiments may also be implemented without these specific details. In addition, in the following descriptions, descriptions of well-known structures and technologies are omitted to avoid unnecessarily obscuring concepts of the present disclosure.

Terms used herein are for the purpose of describing specific embodiments only and are not intended to limit the present disclosure. The terms "including", "containing", etc. used herein indicate the presence of the feature, step, operation and/or component, but do not exclude the presence or addition of one or more other features, steps, operations or components.

All terms used herein (including technical and scientific terms) have the meanings generally understood by those skilled in the art, unless otherwise defined. It should be noted that the terms used herein shall be interpreted to have meanings consistent with the context of this specification, and shall not be interpreted in an idealized or overly rigid manner.

In a case of using the expression similar to "at least one selected from A, B, and C", it should be explained according to the meaning of the expression generally understood by those skilled in the art (for example, "a system including at least one selected from A, B, and C" should include but not be limited to a system including A alone, a system including B alone, a system including C alone, a system including A and B, a system including A and C, a system including B and C, and/or a system including A, B and C). In a case of using the expression similar to "at least one selected from A, B, or C", it should be explained according to the meaning of the expression generally understood by those skilled in the art (for example, "a system including at least one selected from A, B, or C" should include but not be limited to a system including A alone, a system including B alone, a system including C alone, a system including A and B, a system including A and C, a system including B and C, and/or a system including A, B and C).

A research on a living tissue element measurement based on an optical method has experienced nearly fifty years of development, and a large number of scientific research institutes and companies have invested great research enthusiasm in this field. Due to a weak absorption of a measured tissue element and a small variation range of a concentration of the measured tissue element of the measured object, a signal of the measured tissue element is generally weak, and the weak signal of the measured tissue element may be easily submerged by an interference such as a change in a measurement condition. Up to now, there has not appeared a solution that may achieve a reliable tissue element measurement. Therefore, the living tissue element measurement is a global problem that needs to be solved. The tissue element may include blood glucose, fat, and white blood cells, etc. The signal of the measured tissue element represents a change in an output light intensity caused by a change in a concentration of the measured tissue element. The measurement condition may include a controllable measurement condition and an uncontrollable measurement condition. The measurement condition may be understood as a condition that affects a transmission path of light.

In a process of implementing concepts of the present disclosure, the inventors found that main causes for the low measurement accuracy in the related art are as follows.

The inventors found that: if a measurement result obtained when arranging a measurement probe close to a blood vessel is compared with a measurement result obtained when arranging the same measurement probe far away from the blood vessel while keeping other conditions unchanged, the measurement result obtained when arranging the measurement probe far away from the blood vessel is better than that obtained when arranging the measurement probe close to the blood vessel. The measurement result may be represented by a relative variation of a light intensity value of exit light received by the measurement probe or a standard deviation of the light intensity value. The less the relative variation of the light intensity value, the better the measurement result, and the less the standard deviation of the light intensity value, the better the measurement result. When studying the causes for the different measurement results, a distance to the blood vessel may reflect a strength of a pulse beat, and the pulse beat is a source of skin jitter. Therefore, it has been found that one of the causes for the low measurement accuracy is the pulse beat.

In a research on the skin jitter, the inventors found that an influence of the pulse beat on the measurement result is substantially due to a fact that the skin jitter caused by the pulse beat affects a transmission path of light in a tissue and then affects an intensity distribution of the exit light in the measurement region. That is, if the influence of the pulse beat on the measurement result is difficult to suppress, it may be difficult to keep consistent transmission path of light in the tissue, which may affect the intensity distribution of the exit light in the measurement region.

Based on the above, in order to minimize an adverse influence of the skin jitter caused by the pulse beat on the measurement result, it is needed to control the transmission path of light in the tissue as much as possible, in other words, it is needed to minimize a change in the transmission path of light in the tissue.

Following this way, embodiments of the present disclosure provide a solution of measuring a tissue element, that is, arranging an anti-jitter portion at a position corresponding to the measurement region so that an average optical path of the exit light received by the measurement probe associated with the anti-jitter portion is maintained within a predetermined optical path range during a skin jitter process at the measurement region. The average optical path is explained as follows. A transmission path of light in a tissue may be expressed by an optical path and a penetration depth. The optical path is used to represent a total distance that light travels in the tissue, and the penetration depth is used to represent a maximum longitudinal distance that light may reach in the tissue. For a determined source-detection distance, the average optical path is used to represent an average value of the optical path of light in the tissue. The source-detection distance represents a radial distance between a center of the incident light and a center of the measurement probe. A description will be given below in conjunction with specific embodiments.

FIG. 1 schematically shows a flowchart of a method of measuring a tissue element according to embodiments of the present disclosure.

As shown in FIG. 1, the method includes operation S110 to operation S220.

In operation S110, a measurement region is irradiated with incident light having at least one predetermined wavelength, where each beam of the incident light is incident on an incident position to form at least one beam of exit light exited from at least one exit position on the measurement region.

According to embodiments of the present disclosure, as different measurement sites have different skin characteristics, including smoothness, hair presence or absence, flatness, skin thickness and softness, etc., it is needed to select an appropriate measurement site according to actual situations, such as a structure of a measurement probe. The measurement site may include at least one selected from a finger, a palm, an arm, a forehead, or an earlobe. The measurement region may be a region on the measurement site.

According to embodiments of the present disclosure, the predetermined wavelength may be a wavelength sensitive to the measured tissue element. A band to which the predetermined wavelength belongs may include an ultraviolet band, a visible light band, a near-infrared band, a mid-infrared band or a far-infrared band. Exemplarily, if the measured tissue element is blood glucose, the predetermined wavelength may be a wavelength sensitive to blood glucose accordingly, which may be specifically 1550 nm or 1609 nm. The incident light may be collimated or non-collimated. There may be one or more incident positions of the incident light.

In operation S120, an anti-jitter portion is arranged at a position corresponding to the measurement region, so that an average optical path of exit light received by a measurement probe associated with the anti-jitter portion is maintained within a predetermined optical path range during a skin jitter process at the measurement region.

According to embodiments of the present disclosure, in order to minimize the adverse influence of the skin jitter caused by the pulse beat on the measurement result so as to minimize the change in the transmission path of light in the tissue, the anti-jitter portion may be arranged at a position corresponding to the measurement region so that the measurement region is subjected to a suitable measurement pressure. When the measurement region is subjected to the suitable measurement pressure, the average optical path of the exit light received by the measurement probe associated with the anti-jitter portion is maintained within the predetermined optical path range during the skin jitter process at the measurement region, that is, the average optical path of the exit light remains unchanged or substantially unchanged during the skin jitter process at the measurement region. The measurement pressure received by the measurement region is determined according to a limit measurement accuracy, which refers to a change in a concentration of a measured tissue element when a light energy variation caused by the change in the concentration of the measured tissue element is equal to a target noise level. The predetermined optical path range may be determined according to a source-detection distance and a tissue optical parameter. The tissue optical parameter may include an absorption coefficient, a scattering coefficient, and an anisotropy factor.

According to embodiments of the present disclosure, an association between the anti-jitter portion and the measurement probe may be understood as that the anti-jitter portion may include the measurement probe and/or a fixing unit. The fixing unit is used to arrange the measurement probe at the position corresponding to the measurement region.

According to embodiments of the present disclosure, it is needed to consider a position of the measurement probe when arranging the anti-jitter portion at an appropriate position corresponding to the measurement region, so as to avoid affecting the exit light acquired by the measurement probe.

Exemplarily, FIG. 2 schematically shows a schematic diagram of a measurement probe receiving exit light when no anti-jitter portion is arranged at a position corresponding to a measurement region according to embodiments of the present disclosure. FIG. 3 schematically shows a schematic diagram of a measurement probe receiving exit light when an anti-jitter portion is arranged at a position corresponding to a measurement region according to embodiments of the present disclosure. Vessel state 1 in FIG. 2 and FIG. 3 represents a vasoconstriction state. The anti-jitter portion is not shown in FIG. 2 and FIG. 3. It should be noted that it is actually needed to ensure that the measurement probe receives the exit light that is incident on incident position A and exited from exit position C during the skin jitter process.

As shown in FIG. 2 and FIG. 3, since no anti-jitter portion is arranged at the position corresponding to the measurement region, a position where the incident light incident on the incident position A is exited changes from the exit position C to exit position B during the skin jitter process, which results in a significant change in the average optical path of the exit light received by the measurement probe. However, in FIG. 3, since the anti-jitter portion is arranged at the position corresponding to the measurement region, the position where the incident light incident on the incident position A is exit may still be maintained at the exit position B during the skin jitter process, so that the average optical path of the exit light received by the measurement probe is maintained within the predetermined optical path range during the skin jitter process at the measurement region. Therefore, by arranging the anti-jitter portion at the position corresponding to the measurement region, it may be ensured that the measurement probe receives the exit light that is incident at the incident position A and exited from the exit position C during the skin jitter process.

According to technical solutions of embodiments of the present disclosure, by arranging the anti-jitter portion at the position corresponding to the measurement region, the average optical path of the exit light received by the measurement probe associated with the anti-jitter portion may be maintained within the predetermined optical path range during the skin jitter process at the measurement region, so that the change in the transmission path of light in the tissue may be minimized and the measurement accuracy may be improved.

According to embodiments of the present disclosure, the measurement pressure received by the measurement region is determined according to the limit measurement accuracy.

According to embodiments of the present disclosure, the limit measurement accuracy refers to the change in the concentration of the measured tissue element when an output light intensity variation caused by the change in the concentration of the measured tissue element is equal to a target noise level. The limit measurement accuracy may be understood as a function of the average optical path. The limit measurement accuracy may be determined by Equation (1).

$$C_{lim} = \frac{1}{|\varepsilon \cdot L \cdot SNR|} \tag{1}$$

where $C_{lim}$ represents a limit measurement accuracy, $\varepsilon$ represents a molar extinction coefficient, L represents an average optical path of the measured tissue element in a target tissue layer, and SNR represents a target signal-to-noise ratio.

According to embodiments of the present disclosure, after the limit measurement accuracy, the target signal-to-noise ratio and the molar extinction coefficient are determined, the average optical path of the measured tissue element in the target tissue layer may be determined according to Equation (1). The corresponding measurement pressure may be determined according to the average optical path of the measured tissue element in the target tissue layer, that is, under the corresponding measurement pressure, the average optical path of the measured tissue element in the target tissue layer is the average optical path determined according to Equation (1).

According to embodiments of the present disclosure, the anti-jitter portion causes a movement amplitude of the skin at the measurement region to be less than or equal to a movement amplitude threshold. Alternatively, a movement pattern of the anti-jitter portion is consistent with a skin jitter pattern at the measurement region.

According to embodiments of the present disclosure, in order to maintain the average optical path of the exit light received by the measurement probe within the predetermined optical path range during the skin jitter process at the measurement region, the anti-jitter portion may have a large mass, so that when the anti-jitter portion is arranged at the position corresponding to the measurement region, it may press the skin jitter at the measurement region, that is, the movement amplitude of the skin at the measurement region is less than or equal to the movement amplitude threshold. The average optical path of the exit light received by the measurement probe may be maintained within the predetermined optical path range during the skin jitter process at the measurement region because a relative position of the measurement probe on the measurement region may be kept unchanged or substantially unchanged if the anti-jitter portion may press the skin jitter at the measurement region, and then the measurement probe may receive the exit light exited from a fixed exit position. Furthermore, during the skin jitter process at the measurement region, the incident position of the incident light may remain unchanged or substantially unchanged relative to the measurement region. In a case that the incident position of the incident light and the exit position of the exit light are determined, it may be ensured as much as possible that the average optical path of the exit light remains unchanged.

In addition to providing an anti-jitter portion with a large mass to press the skin jitter at the measurement region, it is also possible to provide an anti-jitter portion with a small mass so that the anti-jitter portion may follow the skin jitter at the measurement region when the anti-jitter portion is arranged at the position corresponding to the measurement region, that is, the movement pattern of the anti-jitter portion is consistent with the skin jitter pattern at the measurement region. The average optical path of the exit light received by the measurement probe may be maintained within the predetermined optical path range during the skin jitter process at the measurement region because a relative position of the measurement probe on the measurement region may be kept unchanged or substantially unchanged if the anti-jitter portion may follow the skin jitter at the measurement region, and then the measurement probe may receive the exit light exited from a fixed exit position. The fixed exit position here means an exit position that remains unchanged or substantially unchanged relative to the measurement region. Furthermore, during the skin jitter process at the measurement region, the incident position of the incident light may remain unchanged or substantially unchanged relative to the measurement region. In a case that the incident position of the incident light and the exit position of the exit light are determined, it may be ensured as much as possible that the average optical path of the exit light remains unchanged.

Figure 4:
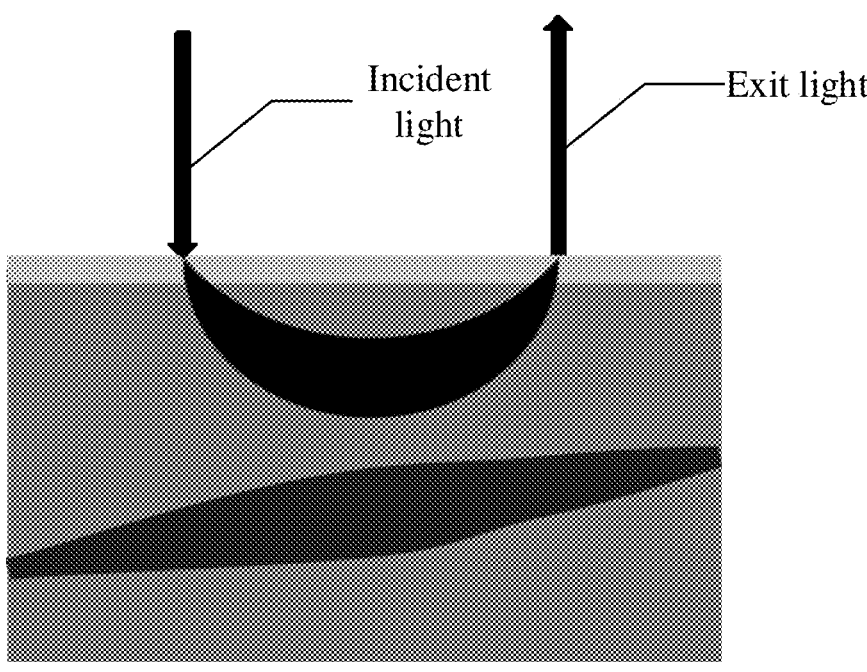
FIG. 4 schematically shows a schematic diagram of maintaining an average optical path of the exit light received by the measurement probe within a predetermined optical path range during a skin jitter process in a case that the anti-jitter portion causes a movement amplitude of a skin at the measurement region to be less than or equal to a movement amplitude threshold according to embodiments of the present disclosure.

Exemplarily, FIG. 4 schematically shows a schematic diagram of maintaining an average optical path of the exit light received by the measurement probe within a predetermined optical path range during a skin jitter process in a case that the anti-jitter portion causes a movement amplitude of a skin at the measurement region to be less than or equal to a movement amplitude threshold according to embodiments of the present disclosure. The measurement probe is not shown in FIG. 4, and the movement amplitude of the skin at the measurement region is close to zero in FIG. 4.

Figure 5:
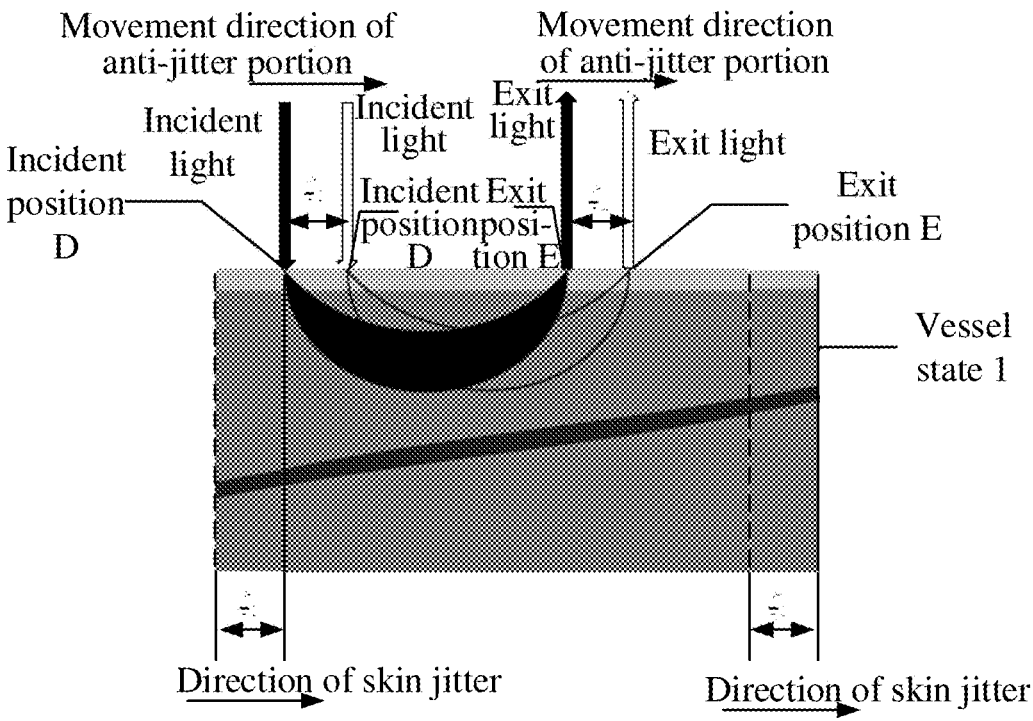
FIG. 5 schematically shows a schematic diagram of maintaining an average optical path of the exit light received by the measurement probe within a predetermined optical path range during a skin jitter process in a case that the anti-jitter portion is consistent with a skin jitter pattern according to embodiments of the present disclosure.

FIG. 5 schematically shows a schematic diagram of maintaining an average optical path of the exit light received by the measurement probe within a predetermined optical path range during a skin jitter process in a case that the anti-jitter portion is consistent with a skin jitter pattern according to embodiments of the present disclosure. During the skin jitter process, the measurement probe (not shown in FIG. 5) may stably receive the exit light that is exited from the exit position B at the measurement region after the incident light is incident on the incident position A at the measurement region. A movement amplitude of the skin is represented by $\xi_1$, and a movement amplitude of the measurement probe is represented by $\xi_2$, $\xi_1 = \xi_2$.

According to embodiments of the present disclosure, a mass of the anti-jitter portion is less than or equal to a mass threshold, so that the movement pattern of the anti-jitter portion is consistent with the skin jitter pattern at the measurement region.

According to embodiments of the present disclosure, in order to keep the movement pattern of the anti-jitter portion consistent with the skin jitter pattern at the measurement region, the anti-jitter portion may have a small mass so that a relative position between the measurement probe and the measurement region remains unchanged.

According to embodiments of the present disclosure, the anti-jitter portion is made of a flexible material.

According to embodiments of the present disclosure, in order to make the anti-jitter portion fit with the skin at the measurement region well, it is possible to use an anti-jitter portion made of a flexible material.

According to embodiments of the present disclosure, the anti-jitter portion includes a measurement probe and/or a fixing unit.

Arranging the anti-jitter portion at the position corresponding to the measurement region may include the following operations.

The fixing unit is arranged directly at the position corresponding to the measurement region, and the measurement probe is not arranged on the fixing unit. Alternatively, the fixing unit is arranged directly at the position corresponding to the measurement region, and the measurement probe is arranged on the fixing unit. Alternatively, the measurement probe is arranged directly at the position corresponding to the measurement region.

According to embodiments of the present disclosure, the anti-jitter portion may include the measurement probe and/or the fixing unit. The fixing unit is used to fix the measurement probe. The fixing unit may be integrated with, partially separated from or completely separated from the measurement probe, that is, the fixing unit may be a component of the measurement probe, or may be independent of the measurement probe, or partially be a component of the measurement probe and partially be independent of the measurement probe.

According to embodiments of the present disclosure, the measurement probe may be arranged at the position corresponding to the measurement region by the fixing unit, or the measurement probe may be arranged directly at the position corresponding to the measurement region. Alternatively, the fixing unit may be arranged directly at the position corresponding to the measurement region, and the measurement probe is not arranged on the fixing unit. In this case, during the tissue element measurement, in order to allow the measurement probe to receive the exit light exited from the exit position at the measurement region, a position of the measurement probe and/or the fixing unit may be adjusted so that the measurement probe is aligned with the measurement region.

The fixing unit may include a fixing seat and a first fitting part, or the fixing unit may include a second fitting part. The first fitting part is used to arrange the fixing seat at the position corresponding to the measurement region, and the fixing seat is used to arrange the measurement probe. The second fitting part is used to arrange the measurement probe at the position corresponding to the measurement region.

If the fixing unit includes the fixing seat and the first fitting part, the fixing seat is separated from the measurement probe, and the first fitting part is integrated with or separated from the fixing seat. If the fixing unit includes the second fitting part, the second fitting part is integrated with or separated from the measurement probe.

According to embodiments of the present disclosure, the fixing unit includes the fixing seat and the first fitting part.

Arranging the fixing unit directly at the position corresponding to the measurement region and arranging the measurement probe on the fixing unit may include the following operations.

The fixing seat is arranged at the position corresponding to the measurement region by the first fitting part. The measurement probe is arranged on the fixing seat.

According to embodiments of the present disclosure, the measurement probe is arranged at the position corresponding to the measurement region by the fixing seat, rather than directly arranged at the position corresponding to the measurement region.

During the tissue element measurement process, if the measurement probe is arranged at the position corresponding to the measurement region by the fixing seat, the fixing seat may be arranged at the measurement region for a long time without leaving the measurement region, and the measurement probe may be arranged on the fixing seat when a measurement is performed and may be detached from the fixing seat when no measurement is performed. Moreover, since the fixing seat is arranged at the position corresponding to the measurement region, it is possible to maintain a good positioning accuracy and reduce the difficulty of positioning the measurement probe when the measurement probe is detached from the fixing seat and then arranged on the fixing seat.

According to embodiments of the present disclosure, the skin state of the skin at the measurement region meets a first predetermined condition in a process of arranging the fixing seat at the position corresponding to the measurement region by the first fitting part.

According to embodiments of the present disclosure, the skin state of the skin at the measurement region meets a second predetermined condition in a process of arranging the measurement probe on the fixing seat.

According to embodiments of the present disclosure, an action of fixing the fixing seat may affect the skin state of the skin at the corresponding position, and then affect the positioning accuracy of the measurement region. In order to ensure the positioning accuracy of the measurement region, it is possible to ensure that the skin state of the skin at the measurement region meets the first predetermined condition in the process of fixing the fixing seat by the first fitting part. The first predetermined condition may refer to that a change in the skin state of the skin at the corresponding position is within a first predetermined range in the process of fixing the fixing seat by the first fitting part. The change in the skin state may include a skin deformation. Accordingly, the first predetermined range may include a first predetermined deformation range.

According to embodiments of the present disclosure, an action of fixing the measurement probe may affect the skin state of the skin at the corresponding position, and then affect the positioning accuracy of the measurement region. In order to ensure the positioning accuracy of the measurement region, it is possible to ensure that the skin state of the skin at the measurement region meets the second predetermined condition in the process of fixing the measurement probe by the fixing seat. The second predetermined condition may refer to that a change in the skin state of the skin at the corresponding position is within a second predetermined range in the process of fixing the measurement probe by the fixing seat. The change in the skin state may include a skin deformation. Accordingly, the second predetermined range may include a second predetermined deformation range.

According to embodiments of the present disclosure, the measurement probe is non-movable on the fixing seat.

According to embodiments of the present disclosure, when the measurement probe is fixed on the fixing seat, there may be a problem of an unstable fixation that may affect the measurement accuracy. In order to solve this problem, it is possible to ensure that the measurement probe does not move on the fixing seat during the tissue element measurement process.

According to embodiments of the present disclosure, the fixing unit includes the second fitting part.

Arranging the measurement probe directly at the position corresponding to the measurement region may include the following operations.

The measurement probe is arranged at the position corresponding to the measurement region by the second fitting part.

According to embodiments of the present disclosure, for the method of arranging the measurement probe at the position corresponding to the measurement region, in addition to the above-mentioned method of arranging the measurement probe at the position corresponding to the measurement region by the fixing seat, it is also possible to adopt a method of directly arranging the measurement probe at the position corresponding to the measurement region, in which the fixing seat is not required, but a cooperation of the second fitting part is required.

It should be noted that the above-mentioned not requiring the fixing seat may include the following two cases. In a first case, the measurement probe is provided with a structure integrated with the measurement probe, which plays a same role as an independent fixing seat. In a second case, the measurement probe is not provided with a structure that plays the same role as an independent fixing seat.

According to embodiments of the present disclosure, the skin state of the skin at the measurement region meets a third predetermined condition in a process of arranging the measurement probe at the position corresponding to the measurement region by the second fitting part.

According to embodiments of the present disclosure, an action of fixing the measurement probe may affect the skin state of the skin at the corresponding position, and then affect the positioning accuracy of the measurement region. In order to ensure the positioning accuracy of the measurement region, it is possible to ensure that the skin state of the skin at the measurement region meets the third predetermined condition in the process of fixing the measurement probe by the second fitting part. The third predetermined condition may refer to that a change in the skin state of the skin at the corresponding position is within a third predetermined range in the process of fixing the measurement probe by the second fitting part. The change in the skin state may include a skin deformation. Accordingly, the third predetermined range may include a third predetermined deformation range.

According to embodiments of the present disclosure, after arranging the anti-jitter portion at the position corresponding to the measurement region, the method may further include the following operations.

The output light intensity corresponding to each beam of the exit light acquired by the measurement probe is obtained. The concentration of the measured tissue element is determined according to at least one output light intensity corresponding to the at least one predetermined wavelength.

According to embodiments of the present disclosure, after the anti-jitter portion is arranged at the position corresponding to the measurement region, a living tissue element measurement may be performed at the measurement region to determine the concentration of the measured tissue element.

Determining the concentration of the measured tissue element according to the at least one output light intensity corresponding to the at least one predetermined wavelength may include the following operations. For each predetermined wavelength in the at least one predetermined wavelength, a first output light intensity and a second output light intensity are determined from at least two output light intensities corresponding to the predetermined wavelength, a differential processing is performed on the first output light intensity and the second output light intensity corresponding to the predetermined wavelength to obtain a differential signal, and the concentration of the measured tissue element is determined according to the differential signal corresponding to each predetermined wavelength.

Performing the differential processing on the first output light intensity and the second output light intensity corresponding to the predetermined wavelength to obtain the differential signal may include the following operations. The first output light intensity and the second output light intensity corresponding to the predetermined wavelength are processed using a differential circuit to obtain the differential signal, or the first output light intensity and the second output light intensity corresponding to the predetermined wavelength are processed using a differential algorithm to obtain the differential signal.

Processing the first output light intensity and the second output light intensity corresponding to the predetermined wavelength using the differential algorithm to obtain the differential signal may include the following operations. A direct differential operation is performed on the first output light intensity and the second output light intensity corresponding to the predetermined wavelength to obtain the differential signal. Alternatively, a logarithmic processing is performed on the first output light intensity and the second output light intensity corresponding to the predetermined wavelength to obtain a first logarithmic light intensity and a second logarithmic light intensity, and a differential operation is performed on the first logarithmic light intensity and the second logarithmic light intensity corresponding to the predetermined wavelength, so as to obtain the differential signal.

According to embodiments of the present disclosure, it is possible to effectively weaken a common mode interference information through the differential processing, thereby improving the measurement accuracy.

According to embodiments of the present disclosure, obtaining the output light intensity corresponding to each beam of the exit light acquired by the measurement probe may include the following operations.

A light intensity value corresponding to each beam of the exit light acquired by the measurement probe is obtained, so as to obtain T output light intensities. The measurement probe is provided with M photosensitive surfaces. Each output light intensity is obtained by processing the light intensity value of the exit light acquired by one or more photosensitive surfaces, and each photosensitive surface is used to acquire the light intensity value of the exit light exited from the exit position within a predetermined anti-jitter range corresponding to the photosensitive surface. $1 \leq T \leq M$.

According to embodiments of the present disclosure, in order to minimize the adverse influence of the skin jitter caused by the pulse beat on the measurement result, the inventors found that a solution of acquiring the light intensity value of the exit light by using a photosensitive surface with a large area (that is, a large-area photosensitive surface) may be adopted to effectively suppress the adverse influence of the pulse beat on the measurement result. That is, the large-area photosensitive surface may effectively suppress the adverse influence caused by the pulse beat. The so-called "large-area photosensitive surface" may be understood as a photosensitive surface with such area that the photosensitive surface may acquire the light intensity value of the exit light exited from an exit position within a predetermined anti-jitter range. The area of the large-area photosensitive surface is continuous. The large-area photosensitive surface is made of a photosensitive material, and it is different from a single-point optical fiber reception and a joint reception of multiple single optical fibers. A description will be given below to explain in detail why the solution of acquiring the output light intensity of the exit light by using the large-area photosensitive surface may be adopted to effectively suppress the adverse influence of the skin jitter caused by the pulse beat on the measurement result.

In the large-area photosensitive surface, a ratio of an area of the photosensitive surface that may stably receive the exit light to the area of the photosensitive surface may be increased, so that a stability of receiving the exit light may be improved, an adverse influence of a change in the intensity distribution of the exit light caused by the pulse beat may be reduced, and then the measurement accuracy may be improved. The stability may be represented by a relative variation of the light intensity value of the exit light received by the photosensitive surface or a standard deviation of the light intensity value. The less the relative variation of the light intensity value, the higher the stability, and the less the standard deviation of the light intensity value, the higher the stability.

Figure 6:
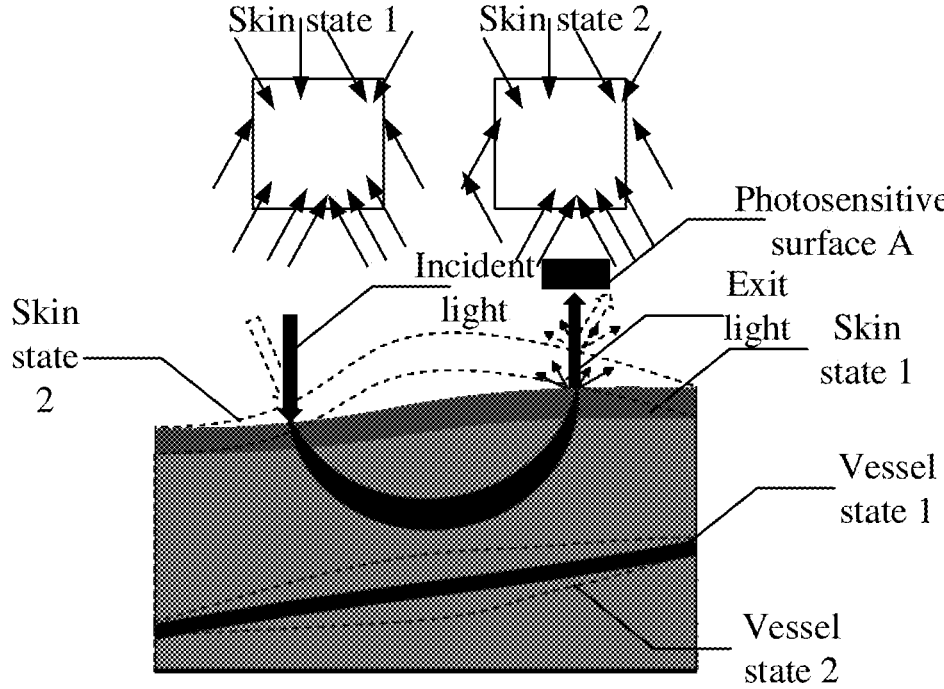
FIG. 6 schematically shows a schematic diagram of receiving exit light using a photosensitive surface with a small area when a jitter occurs according to embodiments of the present disclosure.
Figure 7:
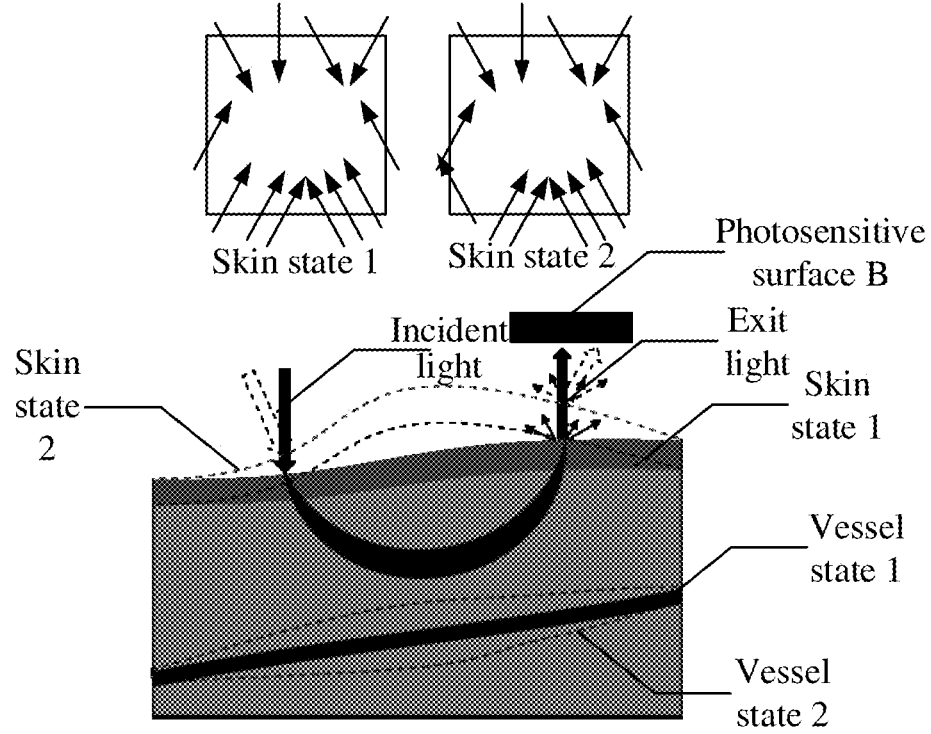
FIG. 7 schematically shows a schematic diagram of receiving exit light using a photosensitive surface with a large area when a jitter occurs according to embodiments of the present disclosure.

Illustratively, the pulse beat may be reflected by a blood vessel state. FIG. 6 schematically shows a schematic diagram of receiving the exit light using a photosensitive surface with a small area when a jitter occurs according to embodiments of the present disclosure. FIG. 7 schematically shows a schematic diagram of receiving the exit light using a photosensitive surface with a large area when a jitter occurs according to embodiments of the present disclosure. The jitter occurs in FIG. 6 is the same as that occurs in FIG. 7. An area of a photosensitive surface A in FIG. 6 is smaller than an area of a photosensitive surface B in FIG. 7, and both the photosensitive surface A and the photosensitive surface B are square photosensitive surfaces. In FIG. 6 and FIG. 7, a blood vessel state 1 represents a vasoconstriction state, a blood vessel state 2 represents a vasodilation state, a skin state 1 represents a skin state corresponding to the blood vessel state 1, and a skin state 2 represents a skin state corresponding to the blood vessel state 2. A change from the skin state 1 to the skin state 2 reflects a skin jitter.

The measurement results obtained using photosensitive surfaces with different areas when the same jitter occurs are compared. The measurement result is represented by the relative variation of the light intensity value of the exit light received by the photosensitive surface within a predetermined time period or the standard deviation of the light intensity value. The relative variation of the light intensity value may be determined by: calculating a difference between a maximum light intensity value and a minimum light intensity value within the predetermined time period, calculating an average value of the exit values within the predetermined time period, calculating a ratio of the difference to the average value, and determining the ratio as the relative variation of the light intensity value. The predetermined time period may be a pulsation cycle.

The measurement results also show that the measurement result obtained by using the photosensitive surface B is better than the measurement result obtained by using the photosensitive surface A whether the measurement result is represented by the relative variation of the light intensity value of the exit light received by the photosensitive surface or the measurement result is represented by the standard deviation of the light intensity value of the exit light received by the photosensitive surface.

As the area of the photosensitive surface B is larger than the area of the photosensitive surface A, it may indicate that the large-area photosensitive surface may improve the stability of receiving the exit light, and then reduce the adverse influence of the change in the intensity distribution of the exit light caused by the jitter, thereby improving a measurement accuracy.

In addition, the output light intensity of the exit light is weak, the change in the output light intensity caused by a change in the concentration of the measured tissue element is also weak, and the method of receiving the exit light adopted in the related art has a low efficiency of receiving the exit light, so that the received output light intensity has a low signal-to-noise ratio, which results in a low measurement accuracy. The large-area photosensitive surface of embodiments of the present disclosure may improve the signal-to-noise ratio of the output light intensity, thereby improving the measurement accuracy. This is because the large-area photosensitive surface may receive a wide range of exit light and improve the efficiency of receiving the exit light, so that the signal-to-noise ratio of the output light intensity may be increased, and the measurement accuracy may be improved.

It should be noted that the large-area photosensitive surface described in embodiments of the present disclosure may achieve a high stability and efficiency of receiving the exit light in a case of a small distance to a surface of the measurement region, that is, in a case that the large-area photosensitive surface is close to the surface of the measurement region. This may not be achieved by using a single-point optical fiber reception and a joint reception of multiple single optical fibers due to a constraint of a numerical aperture of the optical fiber and a limitation of a state change of the optical fiber. The state of the optical fiber is easily affected by an environment, and the state change of the optical fiber has a great influence on the stability of receiving the exit light.

In order to improve the measurement accuracy, it is needed to ensure that each photosensitive surface may acquire the light intensity value of the exit light exited from the exit position within the predetermined anti-jitter range corresponding to the photosensitive surface, which requires the area of the photosensitive surface to be as large as possible. Each photosensitive surface has a corresponding predetermined anti-jitter range, and different photosensitive surfaces correspond to the same or different predetermined anti-jitter ranges. A description will be given below with examples to illustrate that the larger the area of the photosensitive surface, the better the effect of suppressing the skin jitter caused by the pulse beat. In the examples, the area of the photosensitive surface A is smaller than the area of the photosensitive surface B, and both the photosensitive surface A and the photosensitive surface B are square photosensitive surfaces.

The photosensitive surface A and the photosensitive surface B are respectively arranged at a same position on the measurement region, which is a position close to the blood vessel. A measurement result obtained by using the photosensitive surface A may be compared with a measurement result obtained by using the photosensitive surface B when other conditions are the same. The measurement result is represented by a relative variation of the light intensity value of the exit light received by the photosensitive surface within a pulsation cycle or a standard deviation of the light intensity value. The method of calculating the relative variation of the light intensity value is as described above, and will not be repeated here. It was found that the relative variation of the light intensity value of the exit light received by the photosensitive surface B is less than the relative variation of the light intensity value of the exit light received by the photosensitive surface A, and the standard deviation of the light intensity value of the exit light received by the photosensitive surface B is less than the standard deviation of the light intensity value of the exit light received by the photosensitive surface A. Therefore, it may be concluded that the measurement result obtained by using the photosensitive surface B is better than the measurement result obtained by using the photosensitive surface A whether the measurement result is represented by the relative variation of the light intensity value of the exit light received by the photosensitive surface or the measurement result is represented by the standard deviation of the light intensity value of the exit light received by the photosensitive surface.

Since the measurement result obtained by using the photosensitive surface B is better than the measurement result obtained by using the photosensitive surface A, and the area of the photosensitive surface B is larger than the area of the photosensitive surface A, it may indicate that the larger the area of the photosensitive surface, the better the effect of suppressing the skin jitter caused by the pulse beat.

According to embodiments of the present disclosure, each photosensitive surface may be provided as a ring photosensitive surface or a non-ring photosensitive surface. The non-ring photosensitive surface may include a sector-ring photosensitive surface, a circular photosensitive surface, a sector photosensitive surface, an elliptical photosensitive surface, or a polygon photosensitive surface. The polygonal photosensitive surface may include a square photosensitive surface, a rectangular photosensitive surface, or a triangular photosensitive surface.

According to embodiments of the present disclosure, each of the M photosensitive surfaces may be used separately, partially in combination, or all in combination. Used in combination means outputting one output light intensity. In embodiments of the present disclosure, a photosensitive surface for outputting one output light intensity is referred to as a homogeneous photosensitive surface. The homogeneous photosensitive surface may include one or more photosensitive surfaces. A condition for using different photosensitive surfaces in combination may be that for each photosensitive surface, an average optical path of the exit light received by the photosensitive surface is within an average optical path range. The average optical path range may be a range that is greater than or equal to a first average optical path threshold and less than or equal to a second average optical path threshold. The first average optical path threshold and the second average optical path threshold may be determined according to an optical path mean value and an optical path change amplitude. The optical path mean value is a mean value calculated according to the average optical paths of the exit light received at the photosensitive positions of the homogeneous photosensitive surface. Exemplarily, if the optical path mean value is a, and the optical path change amplitude is ±30%, then the first average optical path threshold may be 0.7a, and the second average optical path threshold may be 1.3a.

According to embodiments of the present disclosure, the homogeneous photosensitive surface may be a ring photosensitive surface or a non-ring photosensitive surface. The homogeneous photosensitive surface being a ring photosensitive surface may include that the homogeneous photosensitive surface includes one photosensitive surface, and the homogeneous photosensitive surface is an independent ring photosensitive surface; or the homogeneous photosensitive surface includes a plurality of photosensitive surfaces, and the homogeneous photosensitive surface is a ring photosensitive surface formed by combining the plurality of photosensitive surfaces. The homogeneous photosensitive surface being a non-ring photosensitive surface may include that the homogeneous photosensitive surface includes one photosensitive surface, and the homogeneous photosensitive surface is an independent non-ring photosensitive surface; or the homogeneous photosensitive surface includes a plurality of photosensitive surfaces, and the homogeneous photosensitive surface is a non-ring photosensitive surface formed by combining the plurality of photosensitive surfaces.

After at least one output light intensity corresponding to the predetermined wavelength is obtained, the at least one output light intensity corresponding to the at least one predetermined wavelength may be processed using an interference suppression method to determine the concentration of the measured tissue element. The interference suppression method may include a differential measurement method. The differential measurement method may include a temporal differential measurement method, a position differential measurement method, or a wavelength differential measurement method. Alternatively, the at least one output light intensity may also be processed using a non-differential measurement method to determine the concentration of the measured tissue element. Each output light intensity may include a diffusely-scattered light intensity or a diffusely-transmitted light intensity.

It should be noted that when the method of arranging the anti-jitter portion in the measurement region has a poor effect of suppressing the change in the transmission path of light in the tissue, that is, the average optical path of the exit light received by the measurement probe is not within the predetermined optical path range during the skin jitter process at the measurement region, a large-area photosensitive surface may be used in cooperation to achieve an effective control on the change in the transmission path of light in the tissue.

According to embodiments of the present disclosure, a ratio of an average optical path of the exit light received by each photosensitive surface in a target tissue layer to a total optical path is greater than or equal to a ratio threshold. The total optical path is a total distance that the exit light travels in the measurement region.

According to embodiments of the present disclosure, a tissue model of the measured object is generally a layered structure, that is, it may be divided into one or more layers. Different tissue layers carry different information of the measured tissue element. In order to improve the measurement accuracy, it is required to ensure that the transmission path of the exit light mainly passes through the tissue layer that carries a rich information of the measured tissue element. A target tissue layer may be understood as the tissue layer that carries a rich information of the measured tissue element, or the tissue layer that is a main source of the measured tissue element. In the following description, a human body is taken as an example of the measured object, and blood glucose is taken as an example of the measured tissue element.

A skin tissue model of the human body may be understood as a three-layer model, including epidermis, dermis and subcutaneous fat layer from outside to inside. The epidermis contains a small amount of interstitial fluid, and does not contain plasma and lymph. The dermis contains a large amount of interstitial fluid, and further contains a large amount of plasma and a small amount of lymph due to the presence of abundant capillaries. The subcutaneous fat layer contains a small amount of cellular fluid, and contains a large amount of plasma and a small amount of lymph due to the presence of blood vessels such as veins and arteries. Therefore, different tissue layers carry different information of the measured tissue element.

Since the epidermis contains a small amount of interstitial fluid, it is not an appropriate source of the blood glucose information. Although the subcutaneous fat layer contains a large amount of plasma and a relatively small amount of interstitial fluid, it is still not an appropriate source of the blood glucose information due to a limitation of the penetration depth of the incident light. The dermis contains abundant capillaries and a large amount of interstitial fluid, and the incident light may easily reach the dermis. Therefore, the dermis may be used as a main source of the blood glucose information. Accordingly, the target tissue layer may be the dermis.

According to embodiments of the present disclosure, the average optical path of the exit light in each tissue layer may be determined according to the optical path and the penetration depth. The average optical path may be understood as a function of the source-detection distance and the tissue optical parameter. The tissue optical parameter may include an absorption coefficient, a scattering coefficient, and an anisotropy factor. A factor affecting the average optical path may include the absorption coefficient, the scattering coefficient, the anisotropy factor, and the source-detection distance.

In order to ensure that the transmission path of the exit light mainly passes through the target tissue layer, it is required to ensure that a ratio of the average optical path of the exit light received by each photosensitive surface in the target tissue layer to the total optical path is greater than or equal to a ratio threshold. The total optical path may be a total distance that the exit light travels in the measurement region, that is, a total distance of a path that the incident light travels from entering the measurement region, travelling in the measurement region, to reaching the exit position. The ratio threshold is related to the tissue optical parameter and the source-detection distance between the center of the photosensitive surface and the center of the incident light.

It should be noted that, since the ratio of the average optical path of the exit light received by the photosensitive surface in the target tissue layer to the total optical path is limited in embodiments of the present disclosure, the area of the photosensitive surface in embodiments of the present disclosure may not be overly large, and it is a large area in an area range.

According to embodiments of the present disclosure, a total area of the homogeneous photosensitive surface is determined according to a tissue structure feature in the measurement region. The homogeneous photosensitive surface includes one or more photosensitive surfaces, and the homogeneous photosensitive surface is used to output one output light intensity.

According to embodiments of the present disclosure, the total area of the homogeneous photosensitive surface may be determined according to the tissue structure feature in the measurement region. The tissue structure feature may be understood as a structure feature of the measurement region.

For example, when the measurement region is a region where three blood vessels intersect, if the homogeneous photosensitive surface is arranged in the region where the three blood vessels intersect, the total area of the homogeneous photosensitive surface is limited to an area of the region where the three blood vessels intersect, that is, the total area of the homogeneous photosensitive surface needs to be determined according to the area of the region where the three blood vessels intersect.

For another example, when the measurement region is a region where a finger is located, if the homogeneous photosensitive surface is arranged in the region where the finger is located, the total area of the homogeneous photosensitive surface is limited by an area of the region where the finger is located, that is, the total area of the homogeneous photosensitive surface needs to be determined according to the area of the region where the finger is located.

It should be noted that the area of the photosensitive surface in embodiments of the present disclosure may be determined according to the tissue structure feature, and an area that is determined according to the tissue structure feature may generally not be overly large. Therefore, the area of the photosensitive surface in embodiments of the present disclosure may not be overly large, and it is a large area in the area range.

According to embodiments of the present disclosure, a ratio of the area of each photosensitive surface to a circumference of the photosensitive surface is greater than or equal to a ratio threshold.

According to embodiments of the present disclosure, the reason why the influence of the skin jitter caused by the pulse beat on the intensity distribution of the exit light on the measurement region may be reduced by maximizing the ratio of the area of the photosensitive surface to the circumference of the photosensitive surface so that the ratio is greater than or equal to the ratio threshold is as follows.

For ease of explanation, the photosensitive surface is divided into two portions, including an edge portion and a non-edge portion (or inner portion). Generally, the jitter mainly affects the exit light acquired by the edge portion, while the non-edge portion is less affected, that is, the non-edge portion may acquire the exit light relatively stably. From another perspective, when the skin jitter occurs, the intensity distribution of the exit light on the measurement region may change slightly. The light intensity value of the exit light received by the edge portion may change greatly with the change in the intensity distribution of the exit light, but most of the exit light at the non-edge portion may be acquired by the photosensitive surface relatively stably, so that the light intensity value of the exit light received by the non-edge portion may remain relatively stable. Therefore, it is possible to maximize a ratio of an area corresponding to the non-edge portion to the area of the photosensitive surface in order to effectively suppress the adverse influence of the skin jitter caused by the pulse beat on the measurement result, and the larger the ratio, the better the effect of reducing the adverse influence. The edge portion may be represented by the circumference of the photosensitive surface, and the non-edge portion may be represented by the area of the photosensitive surface. Thus, the ratio of the area of the photosensitive surface to the circumference of the photosensitive surface is required to be as large as possible.

For example, a photosensitive surface 1 is a circular photosensitive surface, and a photosensitive surface 2 is a square photosensitive surface. In a case of a same circumference, since the area of the photosensitive surface 1 is larger than the area of the photosensitive surface 2, the ratio of the area of the photosensitive surface 1 to the circumference of the photosensitive surface 1 is greater than the ratio of the area of the photosensitive surface 2 to the circumference of the photosensitive surface 2. Therefore, the effect of the photosensitive surface 1 reducing the adverse influence is better than the effect of the photosensitive surface 2 reducing the adverse influence.

It should be noted that the description for the ratio of the area of the photosensitive surface to the circumference of the photosensitive surface being greater than or equal to the ratio threshold is given on the basis of meeting the condition that the area of the photosensitive surface is greater than or equal to the area threshold. For most shapes of photosensitive surfaces, if the ratio of the area of the photosensitive surface to the circumference of the photosensitive surface is greater than or equal to the ratio threshold, a size of the area of the photosensitive surface is actually limited, because for most shapes of figures, the ratio of the area to the circumference of the figure has a positive correlation with the size of the area, that is, the greater the ratio of the area to the circumference of the figure, the larger the area of the figure.

For example, in a case of a circle, an area of the circle is $\pi R^2$, and a ratio of the area to the circumference of the circle is R/2, where R represents a radius. The ratio of the area to the circumference of the circle is only related to the radius, and the size of the area of the circle is only related to the radius. Therefore, the ratio of the area to the circumference of the circle has a positive correlation with the size of the area. If the ratio of the area to the circumference of the circle is limited, the size of the area of the circle is also limited. For another example, in a case of a square, an area of the square is $a^2$, and a ratio of the area to the circumference of the square is a/4, where a represents a side length. The ratio of the area to the circumference of the square is only related to the side length, and the size of the area of the square is only related to the side length. Therefore, the ratio of the area to the circumference of the square has a positive correlation with the size of the area. If the ratio of the area to the circumference of the square is limited, the size of the area of the square is also limited.

According to embodiments of the present disclosure, the ratio threshold is greater than or equal to 0.04 mm.

The area of the photosensitive surface in the present disclosure is a relatively large area, that is, the area of the photosensitive surface is a large area within an area range. A description will be given below for this case.

First, the area of the photosensitive surface may not be too small. The large-area photosensitive surface in embodiments of the present disclosure refers to a photosensitive surface with such area that the photosensitive surface may acquire the light intensity value of the exit light exited from the exit position within the predetermined anti-jitter range. Therefore, the large-area photosensitive surface in embodiments of the present disclosure has a large area used to achieve anti-jitter. Furthermore, the ratio of the area of the photosensitive surface to the circumference of the photosensitive surface may be used to indicate that the area of the photosensitive surface allows the photosensitive surface to acquire the light intensity value of the exit light exited from the exit position within the predetermined anti-jitter range, and the ratio of the area to the circumference of the photosensitive surface generally has a positive correlation with the area of the photosensitive surface. Therefore, if the ratio of the area to the circumference of the photosensitive surface is greater than or equal to the ratio threshold, the size of the area of the photosensitive surface is also actually limited, that is, it is also limited that the area of the photosensitive surface may not be too small by limiting that the ratio of the area to the circumference of the photosensitive surface is greater than or equal to the ratio threshold.

Second, the area of the photosensitive surface may not be overly large. In embodiments of the present disclosure, it is required that the ratio of the average optical path of the exit light received by the photosensitive surface in the target tissue layer to the total optical path is greater than or equal to the ratio threshold, and/or the area of the photosensitive surface is determined according to the tissue structure feature, so that the area of the photosensitive surface may not be overly large.

Therefore, the area of the photosensitive surface in embodiments of the present disclosure is a relatively large area, that is, a large area within the area range.

In addition, there may be a case that the photosensitive surface has a large area and also has a large circumference, so that the ratio of the area of the photosensitive surface to the circumference of the photosensitive surface is small, that is, the ratio of the area of the photosensitive surface to the circumference of the photosensitive surface is less than the ratio threshold. Therefore, it is possible that a photosensitive surface having a large absolute area does not meet the anti-jitter requirement. There may also be a case that the photosensitive surface has a small area and a large circumference, so that the ratio of the area of the photosensitive surface to the circumference of the photosensitive surface is less than the ratio threshold. Therefore, a photosensitive area having a very small area may not meet the anti-jitter requirement.

According to embodiments of the present disclosure, the photosensitive surface is in contact or non-contact with a surface of the measurement region.

According to embodiments of the present disclosure, a form of the tissue element measurement may include a contact measurement and a non-contact measurement. The contact measurement may be implemented to prevent interference light from being received by the photosensitive surface, thereby further improving the measurement accuracy. The non-contact measurement may be implemented to avoid an influence of an interference factor such as temperature and pressure on the measurement, thereby further improving the measurement accuracy.

If the photosensitive surface is arranged in contact with the surface of the measurement region, it may be considered that the form of the tissue element measurement is the contact measurement. If the photosensitive surface is arranged in non-contact with the surface of the measurement region, it may be considered that the form of the tissue element measurement is the non-contact measurement.

According to embodiments of the present disclosure, a distance between the photosensitive surface and the surface of the measurement region is less than or equal to a distance threshold, and the efficiency of the photosensitive surface receiving the exit light is greater than or equal to an efficiency threshold.

According to embodiments of the present disclosure, since the photosensitive surface is made of a large-area photosensitive material and photosensitive positions on the photosensitive surface are continuous, a wide range of output light intensity may be received, and the efficiency of light may be improved. Based on this, the efficiency of light may be greater than or equal to the efficiency threshold even when the photosensitive surface is close to the surface of the measurement region, that is, when the distance between the photosensitive surface and the surface of the measurement region is less than or equal to the distance threshold.

According to embodiments of the present disclosure, each photosensitive surface includes a ring photosensitive surface or a non-ring photosensitive surface, and different photosensitive surfaces have the same or different shapes.

According to embodiments of the present disclosure, each photosensitive surface may be made of a photosensitive material. The ring photosensitive surface may avoid a problem of an orientation positioning, and may also achieve a large area design within a small source-detection distance range. It should be noted that the source-detection distance is generally an important physical quantity in the living tissue element measurement, and it is very meaningful to achieve a larger area design within a small source-detection distance.

According to embodiments of the present disclosure, in some cases, using a non-ring photosensitive surface has the following beneficial effects.

In a first aspect, due to the influence of the measurement region on the measurement result, a photosensitive surface arranged in a measurement region conducive to the measurement may generally obtain a better measurement result than a photosensitive surface arranged in a measurement region interfering with the measurement. Therefore, the photosensitive surface may be arranged at an appropriate position according to the tissue structure feature. The non-ring photosensitive surface may easily avoid the measurement region that interferes with the measurement, such as a blood vessel or a wound region. Therefore, a good effect may be achieved by using the non-ring photosensitive surface.

In a second aspect, due to the non-uniformity of the tissue, the same incident light may have different transmission paths in the tissue, and then the exit light exited from different exit positions correspond to different average optical paths. Taking blood glucose as an example of the measured tissue element, a main source of a blood glucose signal is generally the dermis. Therefore, it is required that the exit light is obtained after the incident light is mainly transmitted in the dermis. Accordingly, there are some requirements for the average optical path corresponding to the exit light.

Assuming that a ring photosensitive surface with a corresponding size is designed according to the requirements for the average optical path, it may be considered that the exit light received at different photosensitive positions of the ring photosensitive surface correspond to substantially similar average optical paths and mainly passes through the dermis. The average optical path is within an average optical path range C. In this case, if the skin tissue is uniform, the above conclusion is in line with an actual situation. However, the skin tissue is usually not uniform, and there is a significant difference in the average optical paths corresponding to the exit light received at different photosensitive positions of the same ring photosensitive surface. For example, the exit light received at some photosensitive positions of the ring photosensitive surface corresponds to substantially similar average optical paths, which are within the average optical path range C, while the average optical paths corresponding to the exit light received at the other photosensitive positions of the ring photosensitive surface are quite different from the above, and are not within the average optical path range C. The average optical path of the exit light being within the average optical path range C may indicate that the exit light mainly passes through the dermis, and the average optical path of the exit light being not within the average optical path range C may indicate that the exit light does not mainly pass through the dermis. Since the ring photosensitive surface outputs one output light intensity, the output light intensity obtained using the ring photosensitive surface may have a low signal quality in a case of uneven skin tissue, thereby affecting the measurement accuracy.

The non-ring photosensitive surface may be arranged according to the actual situation. For the above example, if the average optical path not within the average optical path range C is within an average optical path range D, then two non-ring photosensitive surfaces may be used. One non-ring photosensitive surface is used to receive the light intensity value of the exit light of which the average optical path is within the average optical path range C, and the other non-ring photosensitive surface is used to receive the light intensity value of the exit light of which the average optical path is within the average optical path range D. The output light intensities of the two non-ring photosensitive surfaces are consistent with the actual situation, which is beneficial to ensure the measurement accuracy.

In a third aspect, when the living tissue element measurement is performed using the pulse wave-based temporal differential measurement method, it is required to make full use of a pulse signal, that is, to maximize a difference between the light intensity in the systole and the light intensity in the diastole. However, most of the ring photosensitive surface may not be located above the blood vessel, and an effect of acquiring the pulse signal may be affected, so that the difference between the light intensity in the systole and the light intensity in the diastole is reduced. Therefore, the difference between the light intensity in the systole and the light intensity in the diastole obtained by using the ring photosensitive surface is less than the difference between the light intensity in the systole and the light intensity in the diastole obtained by using the non-ring photosensitive surface.

In a fourth aspect, due to a tissue non-uniformity and the influence of the change in the physiological background on the exit light, there may be a difference between the average optical paths of the exit light received at different photosensitive surfaces having a same source-detection distance from the center of the incident light. Therefore, a differential operation may be performed on the output light intensities acquired at different photosensitive surfaces having the same source-detection distance from the center of the incident light for the tissue element measurement. The above may be implemented by the non-ring photosensitive surface, that is, for the same source-detection distance, it is possible to separately arrange at least two non-ring photosensitive surfaces with the center of the incident light as a center, so as to output two output light intensities.

In a fifth aspect, the manufacturing process is not difficult and the manufacturing cost is not high.

Figure 8:
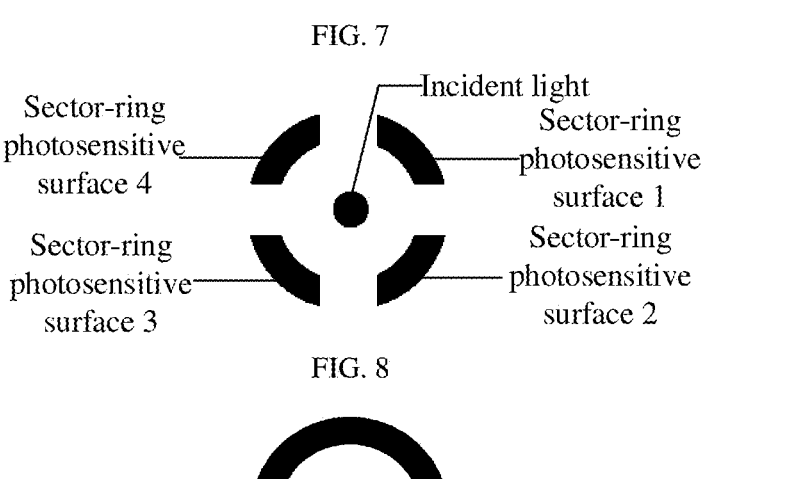
FIG. 8 schematically shows a schematic diagram of a differential measurement according to embodiments of the present disclosure.

The fourth aspect will be described below with reference to FIG. 8. FIG. 8 schematically shows a schematic diagram of a differential measurement according to embodiments of the present disclosure. As shown in FIG. 8, four sector-ring photosensitive surfaces are shown in FIG. 8, including a sector-ring photosensitive surface 1, a sector-ring photosensitive surface 2, a sector-ring photosensitive surface 3, and a sector-ring photosensitive surface 4. The four sector-ring photosensitive surfaces are separately used, and each sector-ring photosensitive surface has a corresponding output light intensity. Centers of the four sector-ring photosensitive surfaces have a same distance from the center of the incident light, that is, the four sector-ring photosensitive surfaces have the same source-detection distance. Due to the tissue non-uniformity, the average optical path corresponding to the exit light received by the sector-ring photosensitive surface 1 is different from the average optical path corresponding to the exit light received by the sector-ring photosensitive surface 2. A differential operation may be performed according to the output light intensity acquired by the sector-ring photosensitive surface 1 and the output light intensity acquired by the sector-ring photosensitive surface 2, so as to perform a differential measurement.

According to embodiments of the present disclosure, the non-ring photosensitive surface includes a sector-ring photosensitive surface, a circular photosensitive surface, a sector photosensitive surface, an elliptical photosensitive surface, or a polygonal photosensitive surface.

According to embodiments of the present disclosure, the polygonal photosensitive surface includes a square photosensitive surface, a rectangular photosensitive surface, or a triangular photosensitive surface.

According to embodiments of the present disclosure, it is possible to design a central angle according to the actual situation, so as to obtain the corresponding sector-ring photosensitive surface, such as a sector-ring photosensitive surface with a central angle of 90°, a sector-ring photosensitive surface with a central angle of 180°, and a sector-ring photosensitive surface with a central angle of 45°.

Figure 9:
FIG. 9 schematically shows a schematic diagram of a ring photosensitive surface according to embodiments of the present disclosure.

According to embodiments of the present disclosure, FIG. 9 schematically shows a schematic diagram of a ring photosensitive surface according to embodiments of the present disclosure. FIG. 10 schematically shows a schematic diagram of a sector-ring photosensitive surface according to embodiments of the present disclosure. FIG. 11 schematically shows a schematic diagram of a circular photosensitive surface according to embodiments of the present disclosure. FIG. 12 schematically shows a schematic diagram of a square photosensitive surface according to embodiments of the present disclosure.

According to embodiments of the present disclosure, each output light intensity being obtained by processing the light intensity value of the exit light acquired by one or more photosensitive surfaces may include the following operations.

One or more photosensitive surfaces are used in combination to output an output light intensity. When each of the one or more photosensitive surfaces is used separately, the light intensity value of the exit light acquired by each photosensitive surface is calculated to obtain an output light intensity.

According to embodiments of the present disclosure, a photosensitive surface for outputting an output light intensity is referred to as a homogeneous photosensitive surface, and the homogeneous photosensitive surface may include one or more photosensitive surfaces. A condition for using different photosensitive surfaces in combination may be that for each photosensitive surface, the average optical path of the exit light received by the photosensitive surface is within the average optical path range. The average optical path range may be a range greater than or equal to a first average optical path threshold and less than or equal to a second average optical path threshold. The first average optical path threshold and the second average optical path threshold may be determined according to the optical path mean value and the optical path change amplitude. The optical path mean value is a mean value calculated according to the average optical paths of the exit light received at the photosensitive positions of the homogeneous photosensitive surface.

The photosensitive surface is generally used in cooperation with an amplification circuit corresponding to the photosensitive surface, so as to output a light intensity value. In order to allow the homogeneous photosensitive surface to output an accurate output light intensity, it is required that a product of a light response rate of each photosensitive surface in the homogeneous photosensitive surface and an amplification factor of the amplification circuit used in cooperation with the photosensitive surface is a predetermined value. When the product of the light response rate of each photosensitive surface and the amplification factor of the amplification circuit used in cooperation with the photosensitive surface is a same predetermined value, the homogeneous photosensitive surface may output one output light intensity. If the product of the light response rate of a photosensitive surface and the amplification factor of the amplification circuit used in cooperation with the photosensitive surface is a different predetermined value, it is needed to adopt a corresponding method so that the product is the same predetermined value.

The homogeneous photosensitive surface outputting one output light intensity may be achieved by a hardware method or a software method.

In a first method, which is the hardware method, cathodes of different photosensitive surfaces in the homogeneous photosensitive surface may be electrically connected to each other, and anodes of different photosensitive surfaces in the homogeneous photosensitive surface may be electrically connected to each other, that is, a common-cathode common-anode electrical connection between different photosensitive surfaces may be achieved. In this case, it is equivalent to connecting different photosensitive surfaces in parallel so that one or more photosensitive surfaces are used in combination to output one output light intensity. It should be noted that the light response rates of different photosensitive surfaces need to be as consistent as possible to obtain an accurate output light intensity.

In a second method, which is the software method, the cathodes of different photosensitive surfaces in the homogeneous photosensitive surface are not connected to each other, and the anodes of different photosensitive surfaces in the homogeneous photosensitive surface are not connected to each other, that is, each photosensitive surface is used separately to output a light intensity value. After the light intensity value corresponding to each photosensitive surface is obtained, a weight summation may be performed on the light intensity values of the photosensitive surfaces in the homogeneous photosensitive surface by using a corresponding algorithm, so as to obtain one output light intensity.

Optionally, the output light intensity corresponding to the homogeneous photosensitive surface may be determined by Equation (2) and Equation (3).

$$I = \sum_{i=1}^{N} \alpha_i I_i \qquad (2)$$

$$\alpha_i = \frac{H}{\beta_i \gamma_i} \qquad (3)$$

26 where I represents the output light intensity corresponding to the homogeneous photosensitive surface, $I_i$ represents the light intensity value corresponding to the photosensitive surface i, $i \in \{1, 2, \ldots, N-1, N\}$, N represents the number of photosensitive surfaces included in the homogeneous photosensitive surface, $$1 \leq N \leq M$$

, M represents a total number of photosensitive surfaces, $\alpha_i$ represents a weighting coefficient corresponding to the photosensitive surface i, H represents the predetermined value, $\beta_i$ represents the light response rate corresponding to the photosensitive surface i, $\gamma_i$ represents the amplification factor of the amplification circuit used in cooperation with the photosensitive surface i.

According to embodiments of the present disclosure, the light spot irradiated with the incident light on the measurement region has a uniform intensity distribution.

According to embodiments of the present disclosure, in order to relax the requirement for the measured object when performing the tissue element measurement so as to ensure the measurement accuracy better, it is possible to adopt a method of ensuring a uniform intensity distribution of the light spot irradiated with the incident light on the measurement region. Furthermore, the more uniform the intensity distribution of the light spot irradiated with the incident light on the measurement region, the lower the requirement for the reproducibility of the controllable measurement condition, and the better the effect of reducing the influence of the uncontrollable measurement condition on the measurement result by using the differential measurement method, thereby ensuring the measurement accuracy better. Moreover, when a measure to obtain a uniform intensity distribution of the light spot irradiated with the incident light on the measurement region is adopted, a light energy of the incident light may be attenuated to a certain extent. However, the tissue element measurement requires that the light energy of the incident light may not be too small. Therefore, it is needed to ensure a minimum attenuation of the light energy of the incident light while ensuring the uniform intensity distribution of the light spot irradiated with the incident light on the measurement region. In addition, if the incident light is transmitted by an optical fiber, the uniform intensity distribution of the light spot of the incident light on the measurement region may also reduce an adverse influence of an optical fiber jitter on the measurement result.

According to embodiments of the present disclosure, an area of the light spot irradiated with the incident light on the measurement region is larger than or equal to a light spot area threshold.

According to embodiments of the present disclosure, in order to relax the requirement for the measured object when performing the tissue element measurement so as to ensure the measurement accuracy better, it is possible to make the area of the light spot irradiated with the incident light on the measurement region larger than or equal to the light spot area threshold. Furthermore, within a certain range, the larger the area of the light spot irradiated with the incident light on the measurement region, the lower the requirement for the reproducibility of the controllable measurement condition, and the better the effect of reducing the influence of the uncontrollable measurement condition on the measurement result by using the differential measurement method, thereby ensuring the measurement accuracy better.

The light spot area threshold may be determined according to actual situation, and is not specifically limited here. In addition, if the incident light is transmitted by an optical fiber, the area of the light spot irradiated with the incident light on the measurement region that is larger than or equal to the light spot area threshold may reduce the adverse influence of the optical fiber jitter on the measurement result.

FIG. 13 schematically shows a block diagram of a device of measuring a tissue element according to embodiments of the present disclosure.

As shown in FIG. 13, a device 1300 of measuring a tissue element includes an anti-jitter portion 1310, which is arranged at a position corresponding to a measurement region so that an average optical path of exit light received by a measurement probe 1320 associated with the anti-jitter portion 1310 is maintained within a predetermined optical path range during a skin jitter process at the measurement region. The exit light is obtained by irradiating the measurement region with incident light having at least one predetermined wavelength. Each beam of the exit light is formed by the incident light incident on an incident position and exited from an exit position on the measurement region.

According to the technical solutions of embodiments of the present disclosure, by arranging the anti-jitter portion at the position corresponding to the measurement region so that the average optical path of the exit light received by the measurement probe associated with the anti-jitter portion is maintained within the predetermined optical path range during the skin jitter process at the measurement region, the change in the transmission path of light in the tissue may be minimized, and the measurement accuracy may be improved.

According to embodiments of the present disclosure, a measurement pressure received by the measurement region is determined according to a limit measurement accuracy.

According to embodiments of the present disclosure, the anti-jitter portion 1310 causes a movement amplitude of a skin at the measurement region to be less than or equal to a movement amplitude threshold. Alternatively, a movement pattern of the anti-jitter portion 1310 is consistent with a skin jitter pattern at the measurement region.

According to embodiments of the present disclosure, a mass of the anti-jitter portion 1310 is less than or equal to a mass threshold, so that the movement pattern of the anti-jitter portion 1310 is consistent with the skin jitter pattern at the measurement region.

According to embodiments of the present disclosure, the anti-jitter portion 1310 is made of a flexible material.

Figure 14:
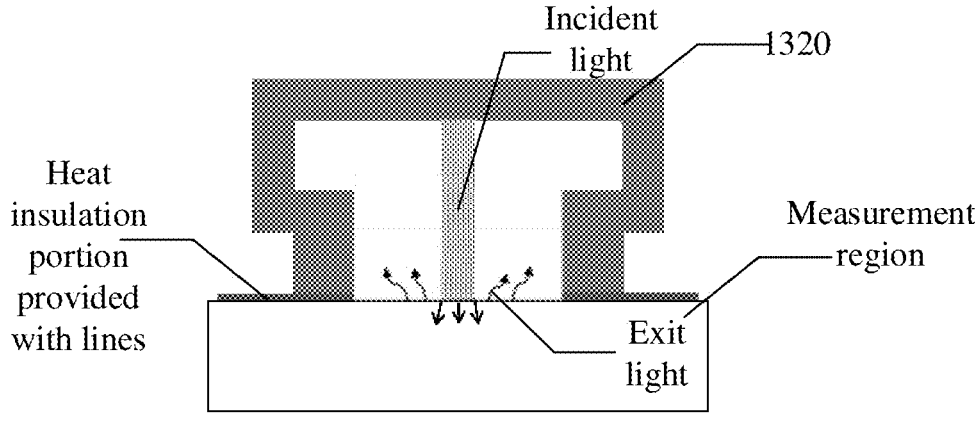
FIG. 14 schematically shows a schematic diagram of arranging a measurement probe directly at a position corresponding to the measurement region according to embodiments of the present disclosure.
Figure 15:
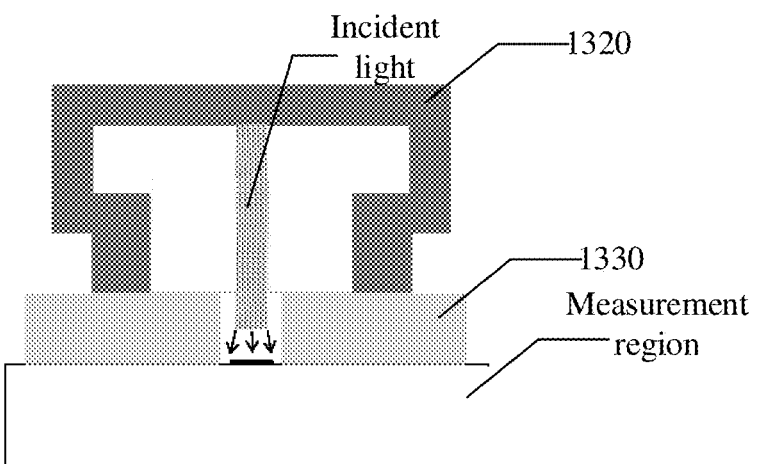
FIG. 15 schematically shows a schematic diagram of fixing a measurement probe by a fixing unit according to embodiments of the present disclosure.

As shown in FIG. 14 and FIG. 15, according to embodiments of the present disclosure, the anti-jitter portion 1310 includes the measurement probe 1320 and/or a fixing unit 1330.

The fixing unit 1330 is arranged directly at the position corresponding to the measurement region, and the measurement probe 1320 is not arranged on the fixing unit. Alternatively, the fixing unit 1330 is arranged directly at the position corresponding to the measurement region, and the measurement probe 1320 is arranged on the fixing unit 1330. Alternatively, the measurement probe 1320 is arranged directly at the position corresponding to the measurement region.

According to embodiments of the present disclosure, FIG. 14 schematically shows a schematic diagram of arranging the measurement probe directly at the position corresponding to the measurement region according to embodiments of the present disclosure. In FIG. 14, a heat insulation portion is further provided between the measurement probe 1320 and the measurement region. The heat insulation portion is provided with lines to allow a skin ventilation and reduce an influence of skin sweating on the measurement result. FIG. 15 schematically shows a schematic diagram of fixing the measurement probe by the fixing unit according to embodiments of the present disclosure.

According to embodiments of the present disclosure, a target region of the fixing unit 1330 is entirely or partially in contact with the measurement region. The target region of the fixing unit 1330 refers to a region of the fixing unit 1330 corresponding to the measurement probe 1320.

Figure 16:
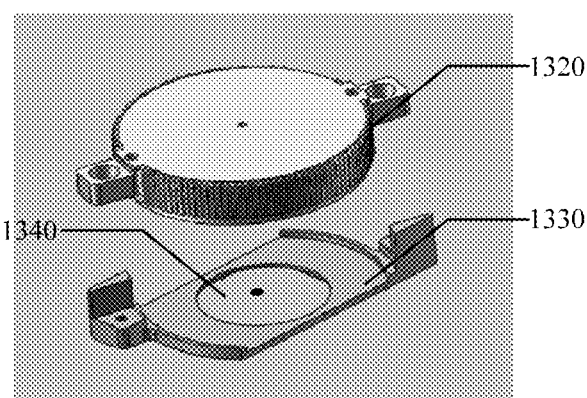
FIG. 16 schematically shows a schematic diagram of providing optical glass on a target region of a fixing unit according to embodiments of the present disclosure.
Figure 17:
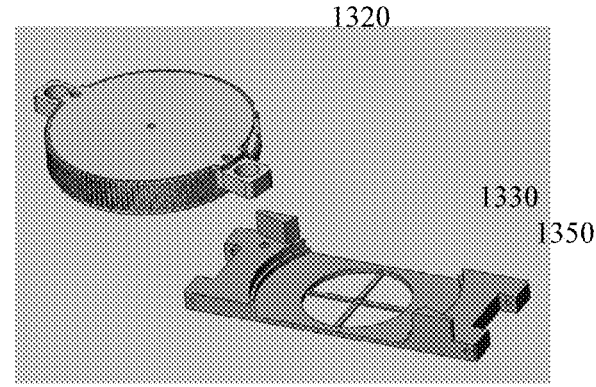
FIG. 17 schematically shows a schematic diagram of providing a frame on a target region of a fixing unit according to embodiments of the present disclosure.

As shown in FIG. 16 and FIG. 17, according to embodiments of the present disclosure, an optical glass 1340 is provided on the target region of the fixing unit 1330. Alternatively, a frame 1350 is provided on the target region of the fixing unit 1330, so that the target region of the fixing unit 1330 is partially in contact with the measurement region.

According to embodiments of the present disclosure, FIG. 16 schematically shows a schematic diagram of providing optical glass on the target region of the fixing unit according to embodiments of the present disclosure, and FIG. 17 schematically shows a schematic diagram of providing a frame on the target region of the fixing unit according to embodiments of the present disclosure.

According to embodiments of the present disclosure, a target surface of the measurement probe 1320 is entirely or partially in contact with the measurement region. The target surface of the measurement probe 1320 refers to a surface close to the measurement region.

Figure 18:
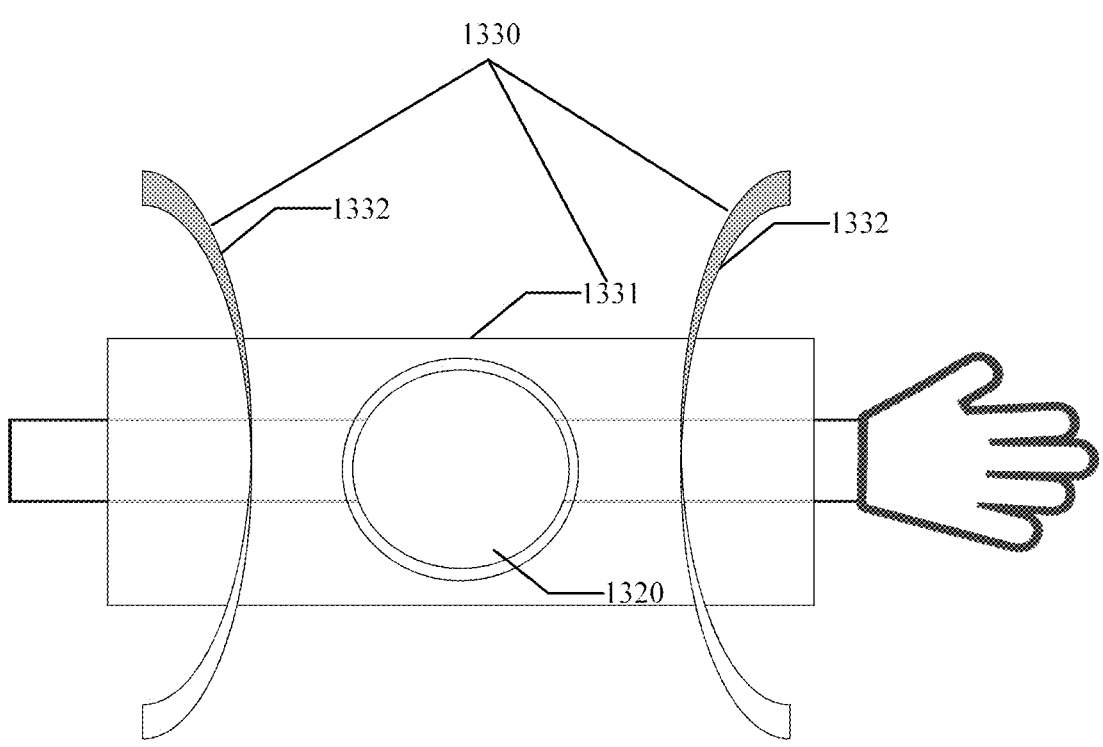
FIG. 18 schematically shows a schematic diagram of a fixing unit according to embodiments of the present disclosure.

As shown in FIG. 18, according to embodiments of the present disclosure, the fixing unit 1330 includes a fixing seat 1331 and a first fitting part 1332. The first fitting part 1332 is used to arrange the fixing seat 1331 at the position corresponding to the measurement region. The fixing seat 1331 is used to fix the measurement probe 1320.

According to embodiments of the present disclosure, a hardness of the first fitting part 1332 includes a first hardness and a second hardness. The first hardness is less than the second hardness. The first hardness is a corresponding hardness in a process of fixing the fixing seat 1331 by the first fitting part 1332, and the second hardness is a corresponding hardness after the fixing seat 1331 is fixed by the first fitting part 1332.

According to embodiments of the present disclosure, in order to enable the first fitting part 1332 to fix the fixing seat 1331, the first fitting part 1332 is required to be rigid. Furthermore, in order to minimize an influence produced when fixing the fixing seat 1331 by the first fitting part 1332, the first fitting part 1332 is required to have a certain flexibility. Therefore, a requirement is put forward on the hardness of the first fitting part 1332.

In order to solve the above problems, it is possible to adopt a method of changing the hardness of the first fitting part 1332, that is, the hardness of the first fitting part 1332 includes the first hardness and the second hardness. The first hardness represents the corresponding hardness in the process of fixing the fixing seat 1331 by the first fitting part 1332, the second hardness represents the corresponding hardness after the fixing seat 1331 is fixed by the first fitting part 1332, and the first hardness is less than the second hardness. In this way, it may not only ensure that the first fitting part 1332 achieves a fixation function, but also minimize the influence produced when fixing the fixing seat 1331 by the first fitting part 1332.

According to embodiments of the present disclosure, the first fitting part 1332 includes a first Velcro or a first elastic belt.

Figure 19:
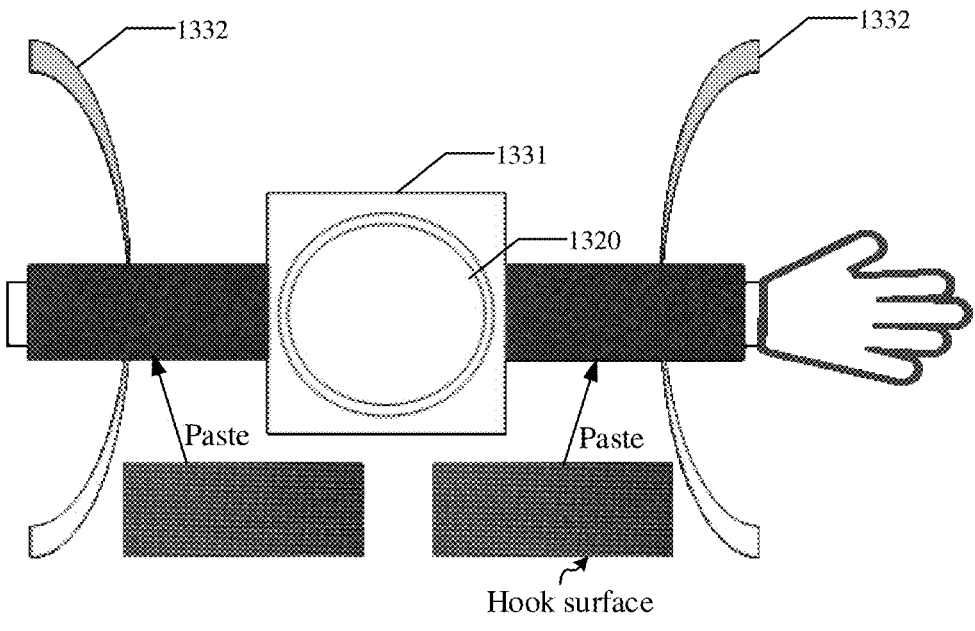
FIG. 19 schematically shows a schematic diagram of a first fitting part according to embodiments of the present disclosure.

Exemplarily, FIG. 19 schematically shows a schematic diagram of the first fitting part according to embodiments of the present disclosure. The first fitting part 1332 in FIG. 19 is a first Velcro. A material of a loop surface of the first Velcro is very soft, so that the influence produced when fixing the fixing seat 1331 by the first fitting part 1332 may be reduced. At this time, the hardness of the first fitting part 1332 is the first hardness. Meanwhile, in order to enable the first fitting part 1332 to achieve the fixation function, after the fixing seat 1331 is fixed by the first fitting part 1332, a hook surface may be pasted on the loop surface to increase the hardness of the first fitting part 1332. At this time, the hardness of the first fitting part 1332 is the second hardness.

According to embodiments of the present disclosure, the corresponding hardness in the process of fixing the fixing seat 1331 by the first fitting part 1332 is the first hardness, which may reduce the influence produced when fixing the fixing seat 1331 by the first fitting part 1332. Therefore, it may be ensured as much as possible that the skin state of the skin at the measurement region meets a first predetermined condition in the process of arranging the fixing seat 1331 at the position corresponding to the measurement region by the first fitting part 1332.

According to embodiments of the present disclosure, the hardness of the first fitting part 1332 is greater than or equal to a first hardness threshold and less than or equal to a second hardness threshold.

According to embodiments of the present disclosure, in order to meet the hardness requirement of the first fitting part 1332, in addition to the method described above, it is also possible to adopt a method of manufacturing the first fitting part 1332 using a material having a hardness greater than or equal to a first hardness threshold and less than or equal to a second hardness threshold, which may also enable the first fitting part 1332 to fix the fixing seat 1331 while minimizing the influence produced when fixing the fixing seat 1331 by the first fitting part 1332. It should be noted that the first hardness threshold and the second hardness threshold may be determined according to actual situations, which are not specifically limited here.

Figure 20:
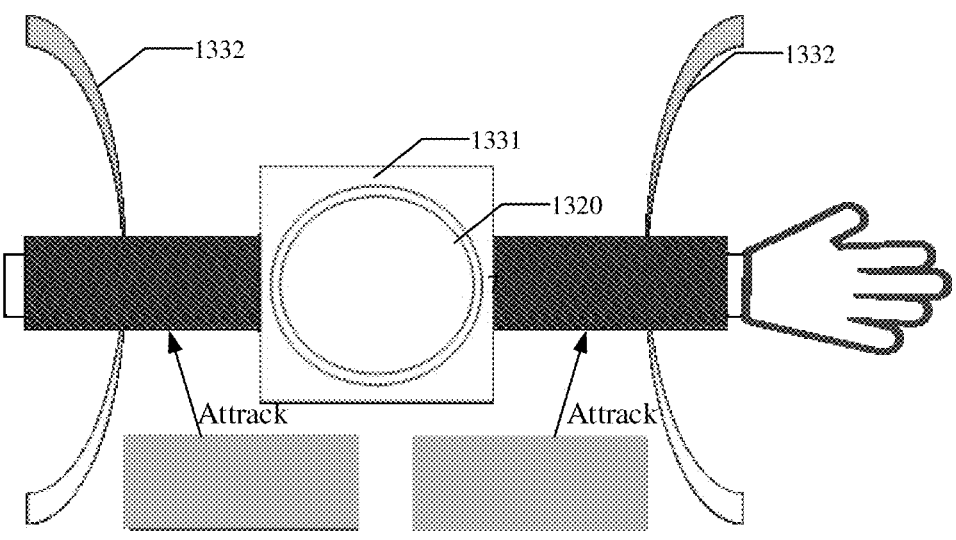
FIG. 20 schematically shows a schematic diagram of another first fitting part according to embodiments of the present disclosure.

As shown in FIG. 20, according to embodiments of the present disclosure, the device 1300 of measuring a tissue element may further include a first magnetic portion 1360. The first fitting part 1332 is entirely or partially a metal hinge, and the first magnetic portion 1360 fits with the first fitting part 1332 to fix the fixing seat 1331.

According to embodiments of the present disclosure, in order to meet the hardness requirement of the first fitting part 1332, in addition to the method described above, it is also possible to adopt a method of designing the first fitting part 1332 to be entirely or partially a metal hinge, which may also enable the first fitting part 1332 to fix the fixing seat 1331 while minimizing the influence produced when fixing the fixing seat 1331 by the first fitting part 1332.

The fixation function may be achieved as follows. After the first fitting part 1332 completes the fixing of the fixing seat 1331, the first magnetic portion 1360 may be attracted to the first fitting part 1332, so that the first magnetic portion 1360 fits with the first fitting part 1332 to fix the fixing seat 1331, thereby achieving the fixation function. Referring to FIG. 20, FIG. 20 schematically shows a schematic diagram of another first fitting part according to embodiments of the present disclosure. The first fitting part 1332 in FIG. 20 is entirely a metal hinge. The first magnetic portion 1360 may be attracted to the first fitting part 1332 after the first fitting part 1332 completes the fixing of the fixing seat 1331. The first magnetic portion 1360 may be a miniature electromagnet.

In addition, since the metal hinge is a ferromagnetic metal and a metal is easy to absorb heat, a direct contact between the metal hinge and the skin may produce a great influence on a skin temperature. In order to avoid an influence of a heat absorption of the metal on the skin temperature, it is possible to place a thermal insulator under the metal hinge. Optionally, the thermal insulator may be flannelette.

The above may be achieved because a good flexibility of the metal hinge may reduce the influence produced when fixing the fixing seat 1331 by the first fitting part 1332. Moreover, after the first fitting part 1332 completes the fixing of the fixing seat 1331, since the first magnetic portion 1360 is attracted on the first fitting part 1332, a cooperation of the two makes the first fitting part 1332 become harder, so that the fixation function may be achieved.

It should be noted that the first fitting part 1332 is entirely or partially a metal hinge, and a good flexibility of the metal hinge may reduce the influence produced when fixing the fixing seat 1331 by the first fitting part 1332. Therefore, it may be ensured as much as possible that the skin state of the skin at the measurement region meets the first predetermined condition in the process of arranging the fixing seat 1331 at the position corresponding to the measurement region by the first fitting part 1332.

According to embodiments of the present disclosure, a surface of the first fitting part 1332 is provided with a hole.

According to embodiments of the present disclosure, the measurement probe 1320 is fixed on the fixing seat 1331 in at least one manner selected from: the measurement probe 1320 being fixed on the fixing seat 1331 by an adhesive tape; the measurement probe 1320 being fixed on the fixing seat 1331 by a fastener; the measurement probe 1320 being fixed on the fixing seat 1331 by a magnetic force; or a friction coefficient between the measurement probe 1320 and the fixing seat 1331 being greater than or equal to a friction coefficient threshold.

According to embodiments of the present disclosure, in order to fix the measurement probe 1320 on the fixing seat 1331 and ensure that the measurement probe 1320 does not move on the fixing seat 1331, at least one of the following methods may be adopted.

In a first method, the measurement probe 1320 may be fixed on the fixing seat 1331 by an adhesive tape. In a second method, the measurement probe 1320 may be fixed on the fixing seat 1331 by a fastener. In a third method, the measurement probe 1320 may be fixed on the fixing seat 1331 by a magnetic force. In a fourth method, the friction coefficient between the measurement probe 1320 and the fixing seat 1331 may be greater than or equal to the friction coefficient threshold. Optionally, a material of the fixing seat 1331 includes rubber, aluminum, or plastic.

According to embodiments of the present disclosure, the fixing unit 1330 includes a second fitting part. The second fitting part is used to arrange the measurement probe at the position corresponding to the measurement region.

According to embodiments of the present disclosure, a hardness of the second fitting part includes a third hardness and a fourth hardness. The third hardness is less than the fourth hardness. The third hardness is a corresponding hardness in a process of fixing the measurement probe 1320 by the second fitting part, and the fourth hardness is a corresponding hardness after the measurement probe 1320 is fixed by the second fitting part.

According to embodiments of the present disclosure, the second fitting part includes a second Velcro or a second elastic belt.

According to embodiments of the present disclosure, the hardness of the second fitting part is greater than or equal to a third hardness threshold and less than or equal to a fourth hardness threshold.

According to embodiments of the present disclosure, the device 1300 of measuring a tissue element further includes a second magnetic portion. The second fitting part is entirely or partially a metal hinge, and the second magnetic portion fits with the second fitting part to fix the measurement probe 1320.

According to embodiments of the present disclosure, a surface of the second fitting part is provided with a hole.

According to embodiments of the present disclosure, for the relevant description of the second fitting part, reference may be made to the above description of the first fitting part 1332, and details will not be repeated here. A difference is that the second fitting part is used to fix the measurement probe 1320.

According to embodiments of the present disclosure, the device 1300 of measuring a tissue element further includes an obtaining module and a processing module. The obtaining module is used to obtain the output light intensity corresponding to each beam of the exit light acquired by the measurement probe. The processing module is used to determine a concentration of the measured tissue element according to at least one output light intensity corresponding to the at least one predetermined wavelength.

According to embodiments of the present disclosure, the measurement probe 1320 is provided with M photosensitive surfaces, and the obtaining module includes an obtaining unit. The obtaining unit is used to obtain a light intensity value corresponding to each beam of the exit light acquired by the measurement probe, so as to obtain T output light intensities. Each output light intensity is obtained by processing the light intensity value of the exit light acquired by one or more photosensitive surfaces, and each photosensitive surface is used to acquire the light intensity value of the exit light exited from an exit position within a predetermined anti-jitter range corresponding to the photosensitive surface.

$$1 \leq T \leq M.$$

According to embodiments of the present disclosure, a ratio of an average optical path of the exit light received by each photosensitive surface in the target tissue layer to a total optical path is greater than or equal to a ratio threshold. The total optical path is a total distance that the exit light travels in the measurement region.

According to embodiments of the present disclosure, a total area of the homogeneous photosensitive surface is determined according to the tissue structure feature in the measurement region. The homogeneous photosensitive surface includes one or more photosensitive surfaces, and the homogeneous photosensitive surface is used to output one output light intensity.

According to embodiments of the present disclosure, a ratio of an area of each photosensitive surface to a circumference of the photosensitive surface is greater than or equal to a ratio threshold.

According to embodiments of the present disclosure, the ratio threshold is greater than or equal to 0.04 mm.

According to embodiments of the present disclosure, the photosensitive surface is in contact or non-contact with the surface of the measurement region.

According to embodiments of the present disclosure, a distance between the photosensitive surface and the surface of the measurement region is less than or equal to a distance threshold, and an efficiency of the photosensitive surface receiving the exit light is greater than or equal to an efficiency threshold.

According to embodiments of the present disclosure, the device 1300 of measuring a tissue element further includes a heat insulation portion arranged between the measurement probe and a surface of the measurement region. A thermal conductivity of the heat insulation portion is within an air thermal conductivity range. The heat insulation portion is used to achieve a non-contact measurement when the device of measuring a tissue element is worn to the measurement region. In addition, by designing the thermal conductivity of the heat insulation portion to be within the air thermal conductivity range, it is possible to reduce a time of reaching a thermal equilibrium of a heat conduction between the device of measuring a tissue element and the measurement region when the device of measuring a tissue element is worn.

According to embodiments of the present disclosure, under the condition that the thermal conductivity of the heat insulation portion is within the air thermal conductivity range, a material of the heat insulation portion may include silica gel, polyvinyl chloride, and the like. In addition, when determining a position of the heat insulation portion, it is required to ensure that the heat insulation portion may not have an adverse influence on a light reception.

According to embodiments of the present disclosure, each photosensitive surface includes a ring photosensitive surface or a non-ring photosensitive surface, and different photosensitive surfaces have the same or different shapes.

According to embodiments of the present disclosure, the non-ring photosensitive surface includes a sector-ring photosensitive surface, a circular photosensitive surface, a sector photosensitive surface, an elliptical photosensitive surface, or a polygonal photosensitive surface.

According to embodiments of the present disclosure, the polygonal photosensitive surface includes a square photosensitive surface, a rectangular photosensitive surface, or a triangular photosensitive surface.

According to embodiments of the present disclosure, the anodes of different photosensitive surfaces among the M photosensitive surfaces are not electrically connected to each other, the anodes of some photosensitive surfaces are electrically connected to each other, or the anodes of all the photosensitive surfaces are electrically connected to each other.

According to embodiments of the present disclosure, each of the M photosensitive surfaces may be used independently. In this case, the anodes of different photosensitive surfaces among the M photosensitive surfaces are not electrically connected to each other.

Some photosensitive surfaces among the M photosensitive surfaces may be used in combination. In this case, the anodes of the different photosensitive surfaces used in combination are electrically connected to each other.

All the photosensitive surfaces of the M photosensitive surfaces may be used in combination. In this case, the anodes of the different photosensitive surfaces used in combination are electrically connected to each other.

Figure 21:
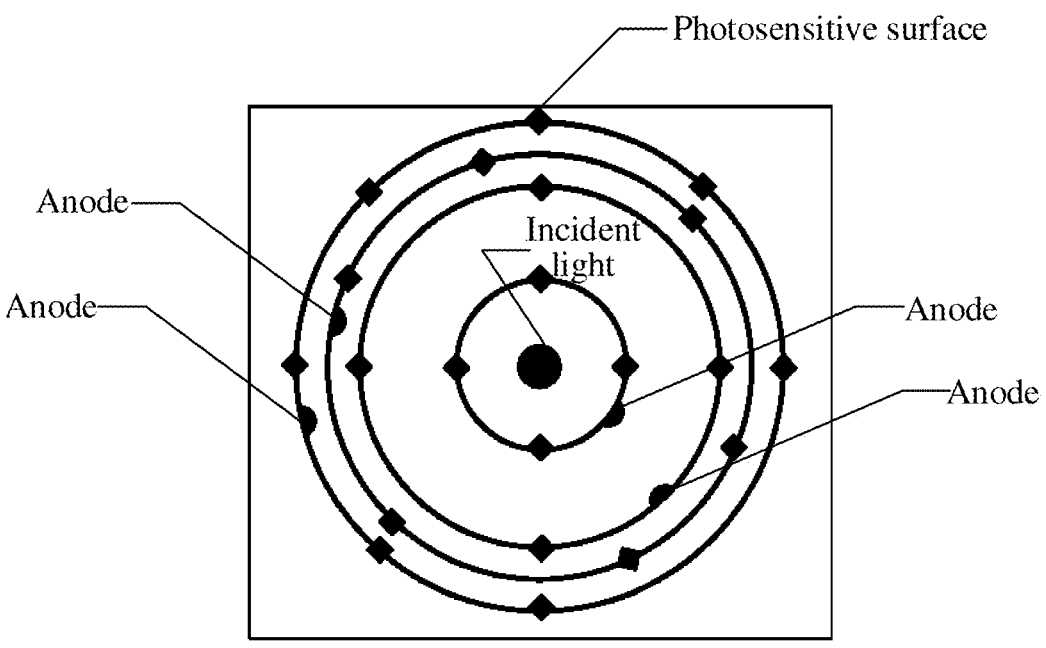
FIG. 21 schematically shows a schematic diagram of an electrical connection of anodes of different photosensitive surfaces according to embodiments of the present disclosure.

According to embodiments of the present disclosure, FIG. 21 schematically shows a schematic diagram of an electrical connection of the anodes of different photosensitive surfaces according to embodiments of the present disclosure. As shown in FIG. 21, the anodes of all the photosensitive surfaces are electrically connected to each other.

According to embodiments of the present disclosure, different parts of a photosensitive surface may be on a same plane or on different planes.

According to embodiments of the present disclosure, the photosensitive surface may be a planar photosensitive surface or a three-dimensional photosensitive surface. If different parts of the photosensitive surface are on the same plane, the photosensitive surface is a planar photosensitive surface. If different parts of the photosensitive surface are on different planes, the photosensitive surface is a three-dimensional photosensitive surface. Whether to use the planar photosensitive surface or the three-dimensional photosensitive surface may be specifically determined according to actual situations, which is not specifically limited here.

Optionally, for a contact measurement, in order to improve the measurement accuracy, it is needed to ensure a good fitting state between a target surface of the photosensitive surface and a skin surface at the measurement region as much as possible. The target surface of the photosensitive surface represents a surface close to the measurement region. A flatness of the skin surface at the measurement region may not be high. If a planar photosensitive surface is used, it may be difficult to achieve a good fitting state between the target surface of the photosensitive surface and the skin surface at the measurement region. The three-dimensional photosensitive surface is a photosensitive surface with different parts on different planes and may be used for the contact measurement. A specific form of the three-dimensional photosensitive surface may be determined according to the tissue structure feature of the measurement region.

Figure 22:
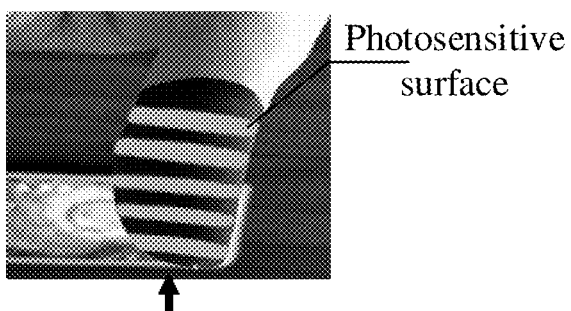
FIG. 22 schematically shows a schematic diagram of a three-dimensional photosensitive surface in a form of a finger cuff according to embodiments of the present disclosure.
Figure 23:
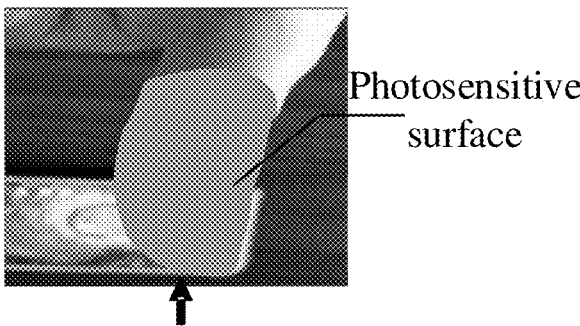
FIG. 23 schematically shows a schematic diagram of another three-dimensional photosensitive surface in a form of a finger cuff according to embodiments of the present disclosure.

FIG. 22 schematically shows a schematic diagram of a three-dimensional photosensitive surface in a form of a finger cuff according to embodiments of the present disclosure. FIG. 23 schematically shows a schematic diagram of another three-dimensional photosensitive surface in a form of a finger cuff according to embodiments of the present disclosure.

Figure 24:
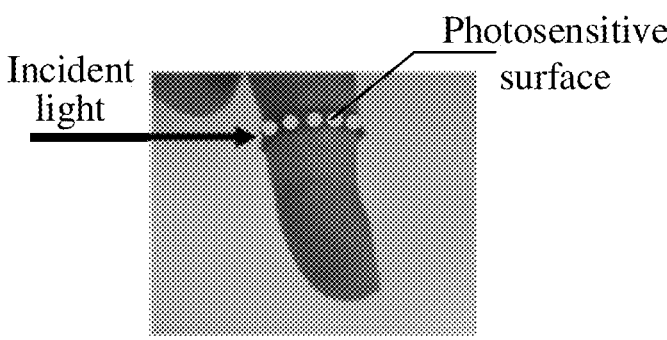
FIG. 24 schematically shows a schematic diagram of a three-dimensional photosensitive surface in a form of a finger ring according to embodiments of the present disclosure.
Figure 25:
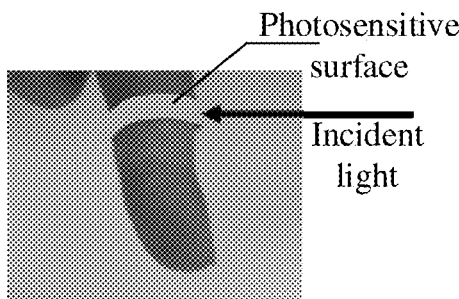
FIG. 25 schematically shows a schematic diagram of another three-dimensional photosensitive surface in a form of a finger ring according to embodiments of the present disclosure.

FIG. 24 schematically shows a schematic diagram of a three-dimensional photosensitive surface in a form of a finger ring according to embodiments of the present disclosure. FIG. 25 schematically shows a schematic diagram of another three-dimensional photosensitive surface in a form of a finger ring according to embodiments of the present disclosure.

Figure 26:
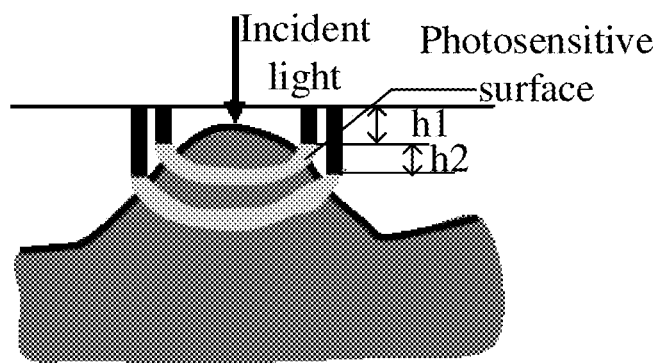
FIG. 26 schematically shows a schematic diagram of a three-dimensional photosensitive surface for an on-arm measurement according to embodiments of the present disclosure.

FIG. 26 schematically shows a schematic diagram of a three-dimensional photosensitive surface for an on-arm measurement according to embodiments of the present disclosure. In FIG. 26, the distances between different parts of the photosensitive surface and the predetermined plane may be determined according to a tissue structure feature of the arm. In FIG. 26, $h_1$ and $h_2$ represent distances between different parts of the photosensitive surface and a predetermined plane.

According to embodiments of the present disclosure, a set of photosensitive surfaces is on a same plane or on different planes, and the set of photosensitive surfaces includes a plurality of photosensitive surfaces.

According to embodiments of the present disclosure, each photosensitive surface included in the set of photosensitive surfaces may be a planar photosensitive surface or a three-dimensional photosensitive surface. If the set of photosensitive surfaces includes a plurality of planar photosensitive surfaces, a photosensitive surface form of three-dimensional photosensitive surface may be presented by the set of photosensitive surfaces by arranging some or all of the plurality of planar photosensitive surfaces on different planes.

Figure 27:
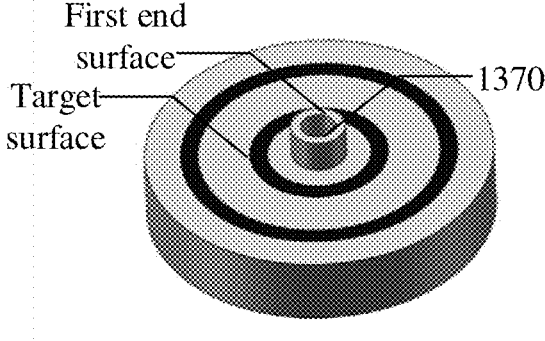
FIG. 27 schematically shows a schematic diagram of providing a first sleeve on a measurement probe according to embodiments of the present disclosure.

As shown in FIG. 27, according to embodiments of the present disclosure, the measurement probe 1320 (not shown in FIG. 27) is provided with a first sleeve 1370. A first end surface of the first sleeve 1370 exceeds the target surface of the measurement probe 1320. The first end surface represents an end surface close to the measurement region, and the target surface of the measurement probe 1320 represents a surface close to the measurement region.

According to embodiments of the present disclosure, in order to shield interference light, the first sleeve 1370 may be arranged on the measurement probe 1320 so that the end surface of the first sleeve 1370 close to the measurement region exceeds the target surface of the measurement probe 1320. The interference light may include surface-reflected light and/or diffracted light.

According to embodiments of the present disclosure, a second end surface and/or an inner region of the first sleeve 1370 are/is provided with a scattering object. The first end surface and the second end surface are two opposite end surfaces, and the inner region includes a partial inner region or an entire inner region.

According to embodiments of the present disclosure, in order to make the light spot irradiated with the incident light on the measurement region have a uniform intensity distribution, it is possible to adopt a method of providing a scattering object at a corresponding part of the first sleeve 1370. The scattering object may include sulfuric acid paper, silica gel, or a target mixture. The target mixture may include a mixture of polydimethylsiloxane and titanium dioxide particles.

Figure 28:
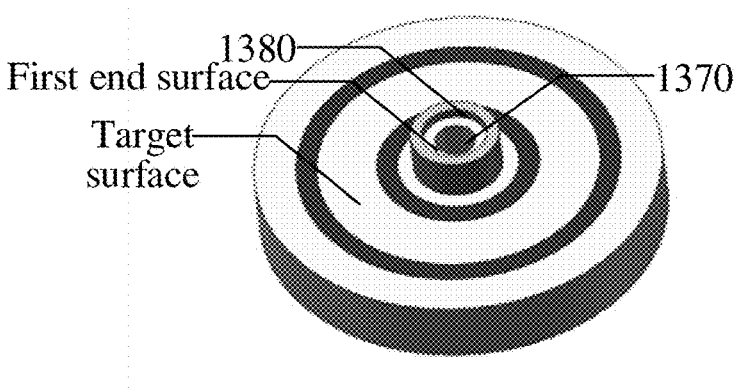
FIG. 28 schematically shows a schematic diagram of providing a second sleeve outside a target region of the first sleeve according to embodiments of the present disclosure.

As shown in FIG. 28, according to embodiments of the present disclosure, the device 1300 of measuring a tissue element further includes a second sleeve 1380 arranged outside a target region of the first sleeve 1370. The target region of the first sleeve 1370 represents a partial region or an entire region of the first sleeve 1370 exceeding the measurement probe 1320.

According to embodiments of the present disclosure, in order to make the light spot irradiated with the incident light on the measurement region as large as possible, it is possible to adopt a method of arranging the second sleeve 1380 outside the target region of the first sleeve 1370.

According to embodiments of the present disclosure, the second sleeve 1380 is provided with a scattering object.

According to embodiments of the present disclosure, if the second sleeve 1380 is provided, it is possible to adopt a method of providing the scattering object at a corresponding part of the second sleeve 1380 in order to make the light spot irradiated with the incident light on the measurement region have a uniform intensity distribution.

According to embodiments of the present disclosure, an inner diameter of the first sleeve 1370 is greater than or equal to an inner diameter threshold.

According to embodiments of the present disclosure, an opening of the first end surface of the first sleeve 1370 is greater than or equal to an opening of the second end surface of the first sleeve 1370.

According to embodiments of the present disclosure, in order to make the light spot irradiated with the incident light on the measurement region as large as possible, it is possible to design that the inner diameter of the first sleeve 1370 is greater than or equal to an inner diameter threshold, and/or the opening of the first end surface of the first sleeve 1370 is greater than or equal to the opening of the second end surface of the first sleeve 1370, that is, the opening of the end surface of the first sleeve 1370 close to the measurement region is greater than or equal to the opening of the end surface of the first sleeve 1370 away from the measurement region.

Figure 30:
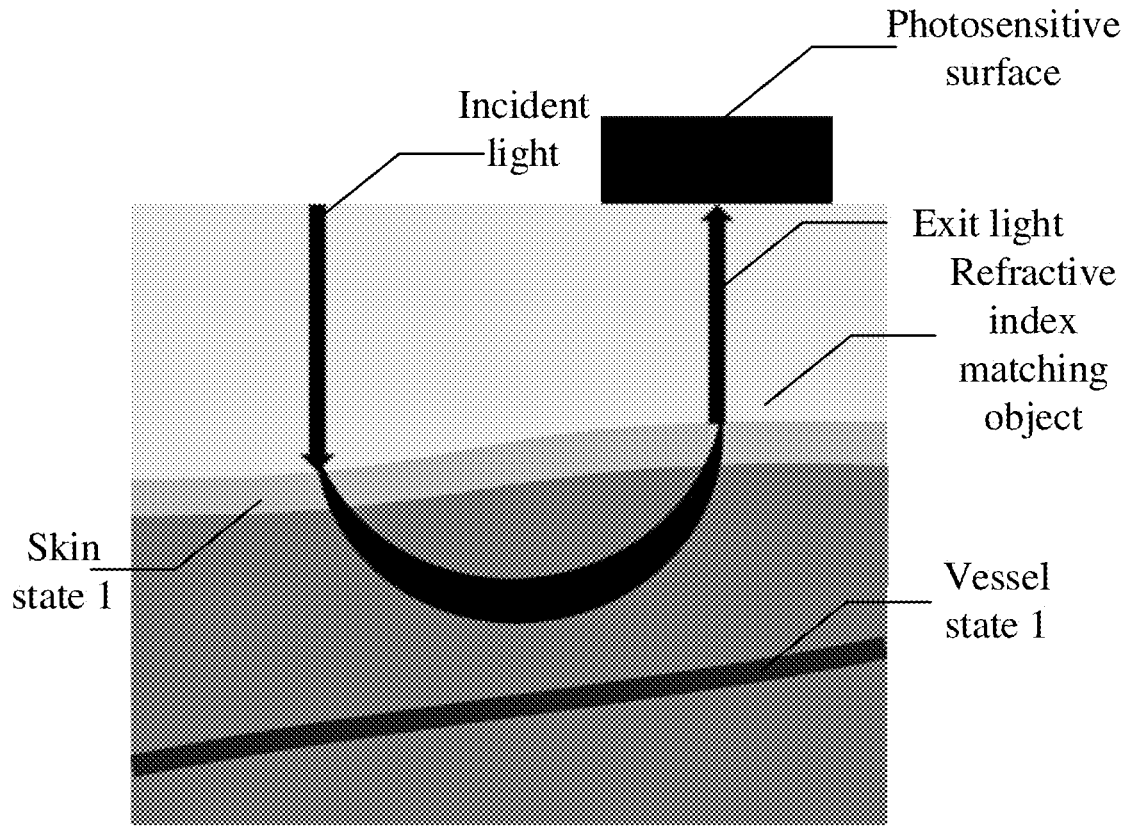
FIG. 30 schematically shows a schematic diagram of a photosensitive surface receiving exit light in a case of a refractive index matching object being filled according to embodiments of the present disclosure.
Figure 31:
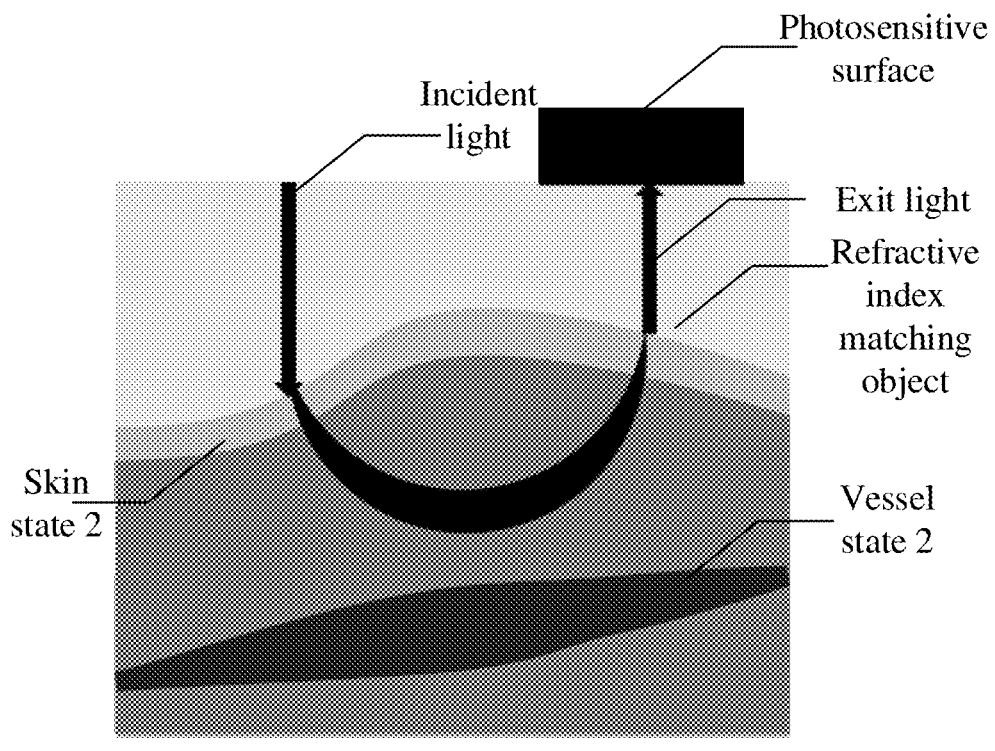
FIG. 31 schematically shows another schematic diagram of a photosensitive surface receiving exit light in a case of a refractive index matching object being filled according to embodiments of the present disclosure.

As shown in FIG. 30 and FIG. 31, according to embodiments of the present disclosure, a refractive index matching object is filled between the photosensitive surface and the measurement region.

According to embodiments of the present disclosure, the skin jitter may cause an unstable surface of the measurement region, and then cause a change in an exit angle of the exit light. Therefore, in order to minimize the adverse influences caused by the skin jitter, it is possible to fill a refractive index matching object between the photosensitive surface and the measurement region to improve the stability and efficiency of the photosensitive surface receiving the exit light.

Figure 29:
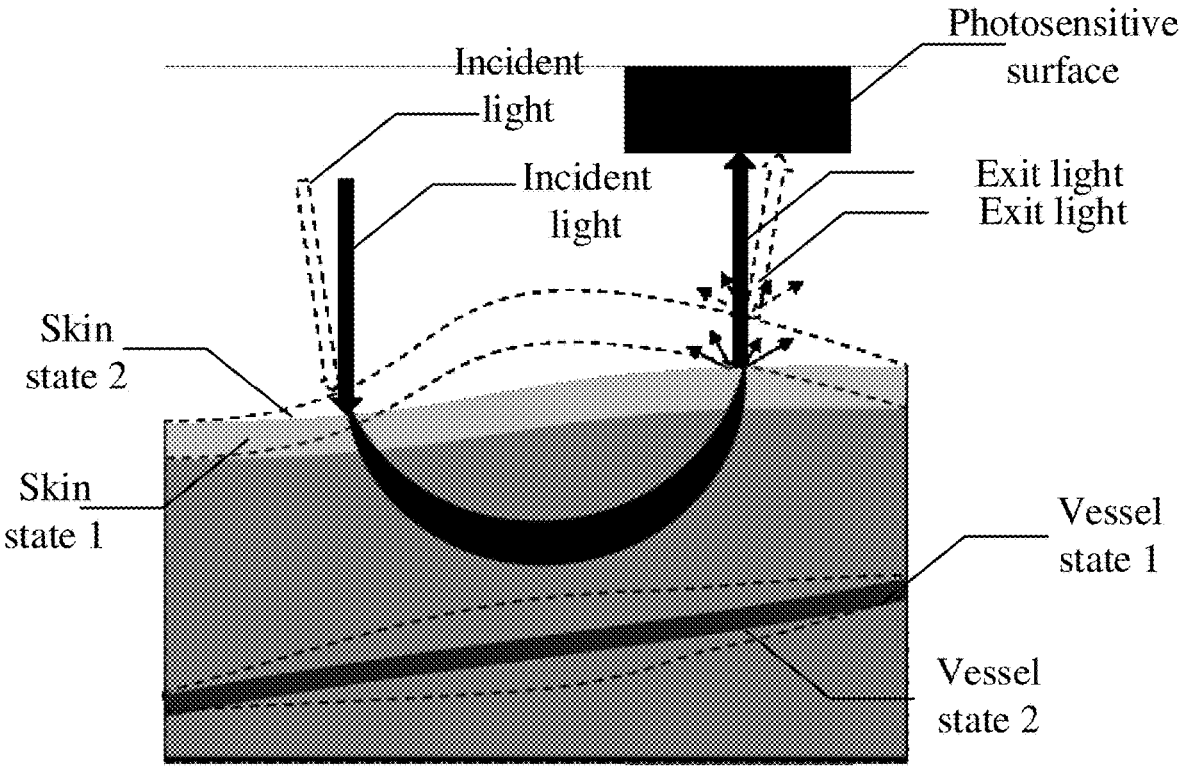
FIG. 29 schematically shows a schematic diagram of a photosensitive surface receiving exit light in a case of no refractive index matching object being filled according to embodiments of the present disclosure.

Illustratively, the pulse beat may be reflected by a blood vessel state. FIG. 29 schematically shows a schematic diagram of the photosensitive surface receiving the exit light in a case of no refractive index matching object being filled according to embodiments of the present disclosure. In FIG. 29, a blood vessel state 1 represents a vasoconstriction state, a blood vessel state 2 represents a vasodilation state, a skin state 1 represents a skin state corresponding to the blood vessel state 1, and a skin state 2 represents a skin state corresponding to the blood vessel state 2. As shown in FIG. 29, the skin jitter may cause an unstable skin surface at the measurement region, and then cause a change in the exit angle of the exit light.

FIG. 30 schematically shows a schematic diagram of the photosensitive surface receiving the exit light in a case of a refractive index matching object being filled according to embodiments of the present disclosure.

FIG. 31 schematically shows another schematic diagram of the photosensitive surface receiving the exit light in a case of a refractive index matching object being filled according to embodiments of the present disclosure.

As shown in FIG. 30 and FIG. 31, the stability and efficiency of the photosensitive surface receiving the exit light may be improve by filling the refractive index matching object between the photosensitive surface and the measurement region.

According to embodiments of the present disclosure, the device 1300 of measuring a tissue element further includes a protective portion. The protective portion is arranged on a target surface of the photosensitive surface and is used to protect the photosensitive surface. The target surface of the photosensitive surface refers to a surface close to the measurement region.

According to embodiments of the present disclosure, in order to protect the photosensitive surface, the protective portion may be provided on the target surface of the photosensitive surface. The protective portion may be made of a transparent and flexible material. The protective portion may include an anti-reflection film or optical glass. A distance between the protective portion and the target surface of the photosensitive surface may be determined according to the material of the protective portion.

For example, if the protective portion is an anti-reflection film, a distance between the anti-reflection film and the target surface of the photosensitive surface may be zero. For another example, if the protective portion is optical glass, a distance between the optical glass and the target surface of the photosensitive surface is greater than or equal to a distance threshold. The distance threshold may be determined according to actual conditions.

Any number of the modules and units according to embodiments of the present disclosure, or at least part of functions of any number of them may be implemented in one module. Any one or more of the modules and units according to embodiments of the present disclosure may be split into a plurality of modules for implementation. Any one or more of the modules and units according to embodiments of the present disclosure may be implemented at least partially as a hardware circuit, such as a field programmable gate array (FPGA), a programmable logic array (PLA), a system on a chip, a system on a substrate, a system on a package, an application specific integrated circuit (ASIC), or may be implemented by hardware or firmware in any other rational manner of integrating or encapsulating the circuit, or may be implemented by any one of three implementation modes of software, hardware and firmware or an appropriate combination thereof. Alternatively, one or more of the modules and units according to embodiments of the present disclosure may be at least partially implemented as a computer program module that may performs the corresponding functions when executed.

For example, any number of the obtaining module and the processing module may be combined into one module/unit for implementation, or any one of the modules/units may be split into a plurality of modules/units. Alternatively, at least part of the functions of one or more of these modules/units may be combined with at least part of the functions of other modules/units and implemented in one module/unit. According to embodiments of the present disclosure, at least one of the obtaining module and the processing module may be implemented at least partially as a hardware circuit, such as a field programmable gate array (FPGA), a programmable logic array (PLA), a system on a chip, a system on a substrate, a system on a package, an application specific integrated circuit (ASIC), or may be implemented by hardware or firmware in any other rational manner of integrating or encapsulating the circuit, or may be implemented by any one of the three implementation modes of software, hardware and firmware or an appropriate combination thereof. Alternatively, at least one of the obtaining module and the processing module may be at least partially implemented as a computer program module that may perform the corresponding functions when executed.

It should be noted that the device of measuring a tissue element in embodiments of the present disclosure corresponds to the description of the method of measuring a tissue element in embodiments of the present disclosure. For the description of the device of measuring a tissue element, reference may be specifically made to the description of the method of measuring a tissue element, which will not be repeated here.

Figure 32:
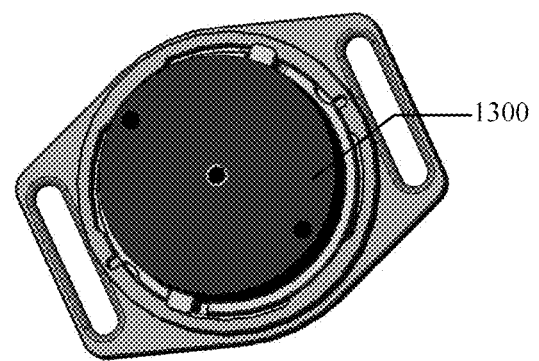
FIG. 32 schematically shows a schematic diagram of a wearable apparatus according to embodiments of the present disclosure.

FIG. 32 schematically shows a schematic diagram of a wearable apparatus according to embodiments of the present disclosure. A wearable apparatus 3200 shown in FIG. 32 is just an example, and should not impose any limitation on a function and a scope of use of the present disclosure.

As shown in FIG. 32, the wearable apparatus 3200 includes the device 1300 of measuring a tissue element.

According to the technical solutions of embodiments of the present disclosure, by arranging the anti-jitter portion at the position corresponding to the measurement region, the average optical path of the exit light received by the measurement probe associated with the anti-jitter portion may be maintained within the predetermined optical path range during the skin jitter process at the measurement region, so that the change in the transmission path of light in the tissue may be minimized and the measurement accuracy may be improved.

According to embodiments of the present disclosure, if the anti-jitter portion has a small mass, the wearable apparatus may have a small mass due to the small mass of the anti-jitter portion, so that the wearable apparatus may fit with the skin at the measurement region well, and the movement pattern of the wearable apparatus may be consistent with the skin jitter pattern at the measurement region.

Figure 33:
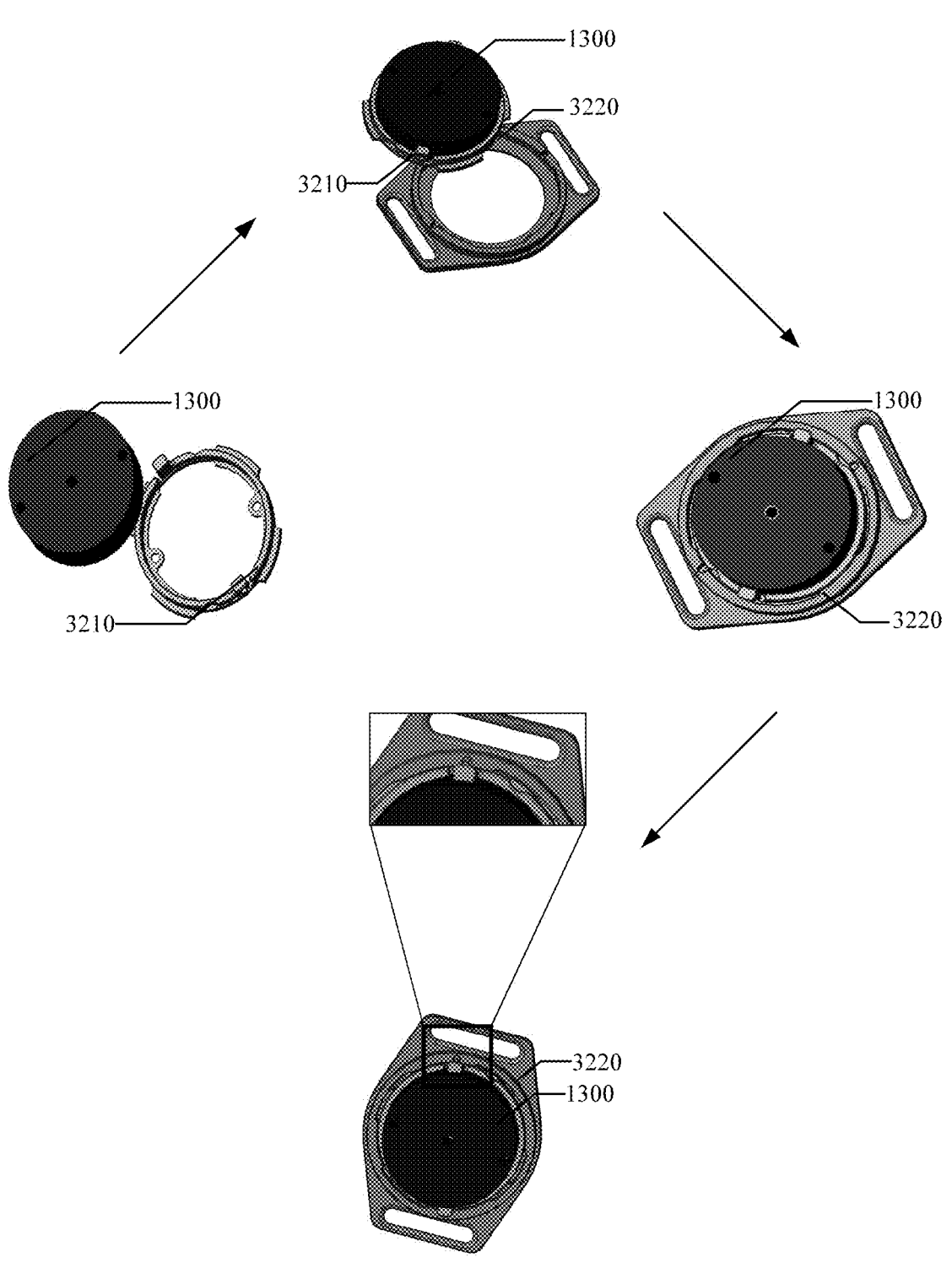
FIG. 33 schematically shows a schematic diagram of an assembly process of the wearable apparatus according to embodiments of the present disclosure.

As shown in FIG. 33, according to embodiments of the present disclosure, the wearable apparatus 3200 further includes a buckle portion 3210 and a body 3220. The buckle portion 3210 and the body 3220 are used in cooperation to fix the device 1300 of measuring a tissue element.

According to embodiments of the present disclosure, FIG. 33 schematically shows a schematic diagram of an assembly process of the wearable apparatus according to embodiments of the present disclosure.

According to embodiments of the present disclosure, for the specific description of the device of measuring a tissue element, reference may be made to the corresponding part above, and details will not be repeated here. In addition, the device of measuring a tissue element includes a processor which may perform various appropriate actions and processes according to a program stored in a read only memory (ROM) or a program loaded from a storage portion into a random access memory (RAM). The processor may include, for example, a general-purpose microprocessor (for example, CPU), an instruction set processor and/or a related chipset and/or a special-purpose microprocessor (for example, an application specific integrated circuit (ASIC)), and the like. The processor may further include an on-board memory for caching purposes. The processor may include a single processing unit or a plurality of processing units for performing different actions of the method flow according to embodiments of the present disclosure.

Various programs and data required for the operation of the device of measuring a tissue element are stored in the RAM. The processor, the ROM and the RAM are connected to each other through a bus. The processor performs various operations of the method flow according to embodiments of the present disclosure by executing the programs in the ROM and/or the RAM. It should be noted that the program may also be stored in one or more memories other than the ROM and the RAM. The processor may also perform various operations of the method flow according to embodiments of the present disclosure by executing the programs stored in the one or more memories.

According to embodiments of the present disclosure, the wearable apparatus may further include an input/output (I/O) interface which is also connected to the bus. The wearable apparatus may further include one or more of the following components connected to the I/O interface: an input part including a keyboard, a mouse, etc.; an output part including a cathode ray tube (CRT), a liquid crystal display (LCD), etc. and a speaker, etc.; a storage part including a hard disk, etc.; and a communication part including a network interface card such as a LAN card, a modem, and the like. The communication part performs communication processing via a network such as the Internet. A drive is also connected to the I/O interface as required. A removable medium, such as a magnetic disk, an optical disk, a magneto-optical disk, a semiconductor memory, and the like, is installed on the drive as required, so that the computer program read therefrom is installed into the storage part.

The present disclosure further provides a computer-readable storage medium, which may be included in the apparatus/device/system described in the above embodiments; or exist alone without being assembled into the apparatus/device/system. The above-mentioned computer-readable storage medium carries one or more programs that perform the methods according to embodiments of the present disclosure when being executed.

According to embodiments of the present disclosure, the computer-readable storage medium may be a non-transitory computer-readable storage medium, for example, may include but not limited to: a portable computer disk, a hard disk, a random access memory (RAM), a read-only memory (ROM), an erasable programmable read-only memory (EPROM) or flash memory, a portable compact disk read-only memory (CD-ROM), an optical storage device, a magnetic storage device, or any suitable combination of the above. In the present disclosure, the computer-readable storage medium may be any tangible medium that contains or stores programs that may be used by or in combination with an instruction execution system, apparatus or device.

For example, according to embodiments of the present disclosure, the computer-readable storage medium may include the above-mentioned ROM and/or RAM and/or one or more memories other than the ROM and RAM.

Embodiments of the present disclosure further include a computer program product, which contains a computer program. The computer program contains program code for performing the method provided by embodiments of the present disclosure.

When the computer program is executed by the processor, the above-mentioned functions defined in the system/device of embodiments of the present disclosure are performed. According to embodiments of the present disclosure, the above-described systems, devices, modules, units, etc. may be implemented by computer program modules.

In an embodiment, the computer program may rely on a tangible storage medium such as an optical storage device and a magnetic storage device. In another embodiment, the computer program may also be transmitted and distributed in the form of signals on a network medium, downloaded and installed through the communication part, and/or installed from the removable medium. The program code contained in the computer program may be transmitted by any suitable medium, including but not limited to a wireless one, a wired one, or any suitable combination of the above.

According to embodiments of the present disclosure, the program code for executing the computer programs provided by embodiments of the present disclosure may be written in any combination of one or more programming languages. In particular, these computing programs may be implemented using high-level procedures and/or object-oriented programming languages, and/or assembly/machine languages. Programming languages include, but are not limited to, Java, C++, Python, "C" language or similar programming languages. The program code may be completely executed on the user computing apparatus, partially executed on the user device, partially executed on the remote computing apparatus, or completely executed on the remote computing apparatus or server. In a case of involving a remote computing apparatus, the remote computing apparatus may be connected to a user computing apparatus through any kind of network, including a local area network (LAN) or a wide area networks (WAN), or may be connected to an external computing apparatus (e.g., through the Internet using an Internet service provider).

The flowcharts and block diagrams in the accompanying drawings illustrate the possible architecture, functions, and operations of the system, method, and computer program product according to various embodiments of the present disclosure. In this regard, each block in the flowcharts or block diagrams may represent a part of a module, a program segment, or a code, which part includes one or more executable instructions for implementing the specified logical function. It should be further noted that, in some alternative implementations, the functions noted in the blocks may also occur in a different order from that noted in the accompanying drawings. For example, two blocks shown in succession may actually be executed substantially in parallel, or they may sometimes be executed in a reverse order, depending on the functions involved. It should be further noted that each block in the block diagrams or flowcharts, and the combination of blocks in the block diagrams or flowcharts, may be implemented by a dedicated hardware-based system that performs the specified functions or operations, or may be implemented by a combination of dedicated hardware and computer instructions. Those skilled in the art may understand that the various embodiments of the present disclosure and/or the features described in the claims may be combined in various ways, even if such combinations are not explicitly described in the present disclosure. In particular, the various embodiments of the present disclosure and/or the features described in the claims may be combined in various ways without departing from the spirit and teachings of the present disclosure. All these combinations fall within the scope of the present disclosure.

Embodiments of the present disclosure have been described above. However, these embodiments are for illustrative purposes only, and are not intended to limit the scope of the present disclosure. Although the various embodiments have been described separately above, this does not mean that measures in the respective embodiments may not be used in combination advantageously. The scope of the present disclosure is defined by the appended claims and their equivalents. Those skilled in the art may make various substitutions and modifications without departing from the scope of the present disclosure, and these substitutions and modifications should all fall within the scope of the present disclosure.

What is claimed is:

1. A device of measuring a tissue element, comprising:
an anti-jitter portion, configured to be arranged at a position corresponding to a measurement region, so that an average optical path of exit light received by a measurement probe associated with the anti-jitter portion is maintained within a predetermined optical path range during a skin jitter process at the measurement region, a measurement pressure received by the measurement region is determined according to a limit measurement accuracy, and the limit measurement accuracy is a change in the concentration of the measured tissue element when a light energy variation caused by the change in the concentration of the measured tissue element is equal to a target noise level, the exit light is obtained by irradiating the measurement region with incident light having at least one predetermined wavelength, and each beam of the exit light is formed by incident light incident on an incident position and exited from an exit position on the measurement region;
an obtaining module configured to obtain an output light intensity corresponding to each beam of the exit light acquired by the measurement probe; and a processing module configured to determine a concentration of a measured tissue element according to at least one output light intensity corresponding to the at least one predetermined wavelength;
the anti-jitter portion causes a movement amplitude of a skin at the measurement region to be less than or equal to a movement amplitude threshold; or
a mass of the anti-jitter portion is less than or equal to a mass threshold, so that the movement pattern of the anti-jitter portion is consistent with the skin jitter pattern at the measurement region.

2. The device according to claim 1, wherein the anti-jitter portion comprises the measurement probe and/or a fixing unit;
the fixing unit is arranged directly at the position corresponding to the measurement region, and the measurement probe is not arranged on the fixing unit; or
the fixing unit is arranged directly at the position corresponding to the measurement region, and the measurement probe is arranged on the fixing unit; or
the measurement probe is arranged directly at the position corresponding to the measurement region.

3. The device according to claim 2, wherein a target region of the fixing unit is entirely or partially in contact with the measurement region, and the target region of the fixing unit is a region corresponding to the measurement probe of the fixing unit,
wherein a target surface of the measurement probe is entirely or partially in contact with the measurement region, and the target surface of the measurement probe is a surface close to the measurement region.

4. The device according to claim 3, wherein the target region of the fixing unit is provided with optical glass; or
the target region of the fixing unit is provided with a frame, so that the target region of the fixing unit is partially in contact with the measurement region.

5. The device according to claim 2, wherein the fixing unit comprises a fixing seat and a first fitting part;
the first fitting part is configured to arrange the fixing seat at the position corresponding to the measurement region, and the fixing seat is configured to fix the measurement probe; or
the fixing unit comprises a second fitting part configured to arrange the measurement probe at the position corresponding to the measurement region.

6. The device according to claim 5, wherein a hardness of the first fitting part comprises a first hardness and a second hardness, the first hardness is less than the second hardness, the first hardness is a corresponding hardness in a process of fixing the fixing seat by the first fitting part, and the second hardness is a corresponding hardness after the fixing seat is fixed by the first fitting part,
wherein a hardness of the second fitting part comprises a third hardness and a fourth hardness, the third hardness is less than the fourth hardness, the third hardness is a corresponding hardness in a process of fixing the measurement probe by the second fitting part, and the fourth hardness is a corresponding hardness after the measurement probe is fixed by the second fitting part.

7. The device according to claim 5, wherein the measurement probe is fixed on the fixing seat by at least one method selected from:
the measurement probe being fixed on the fixing seat by an adhesive tape;
the measurement probe being fixed on the fixing seat by a fastener;

the measurement probe being fixed on the fixing seat by a magnetic force; or a friction coefficient between the measurement probe and the fixing seat being greater than or equal to a friction coefficient threshold.

8. The device according to claim 1, wherein the measurement probe is provided with M photosensitive surfaces; and wherein the obtaining module comprises:

an obtaining unit configured to obtain a light intensity value corresponding to each beam of the exit light acquired by the M photosensitive surfaces, so as to obtain T output light intensities, wherein each of the T output light intensities is obtained by processing the light intensity value of the exit light acquired by one or more of the M photosensitive surfaces, and each of the M photosensitive surfaces is configured to acquire the light intensity value of the exit light exited from an exit position within a predetermined anti-jitter range corresponding to the photosensitive surface, $$1 \le T \le M$$

9. The device according to claim 8, wherein a ratio of an average optical path of the exit light received by each photosensitive surface in a target tissue layer to a total optical path is greater than or equal to a ratio threshold, and the total optical path is a total distance that the exit light travels in the measurement region.

10. The device according to claim 8, wherein a total area of a homogeneous photosensitive surface is determined according to a tissue structure feature in the measurement region, the homogeneous photosensitive surface comprises one or more photosensitive surfaces, and the homogeneous photosensitive surface is configured to output one output light intensity.

11. The device according to claim 8, wherein a ratio of an area of each photosensitive surface to a circumference of the photosensitive surface is greater than or equal to a ratio threshold, wherein the ratio threshold is greater than or equal to 0.04 mm.

12. The device according to claim 8, wherein a distance between the photosensitive surface and the surface of the measurement region is less than or equal to a distance threshold, and an efficiency of the photosensitive surface receiving the exit light is greater than or equal to an efficiency threshold.

13. The device according to claim 1, wherein the measurement probe is provided with a first sleeve; and wherein a first end surface of the first sleeve exceeds a target surface of the measurement probe, the first end surface represents an end surface close to the measurement region, and the target surface of the measurement probe represents a surface close to the measurement region.

14. The device according to claim 13, wherein a second end surface and/or an inner region of the first sleeve are/is provided with a scattering object, the first end surface and the second end surface are opposite end surfaces, and the inner region comprises a partial inner region or an entire inner region.

15. The device according to claim 13, further comprising a second sleeve outside a target region of the first sleeve, wherein the target region of the first sleeve is a partial region or an entire region of the first sleeve exceeding the target surface of the measurement probe.

16. A wearable apparatus, comprising the device of measuring a tissue element according to claim 1.

17. A method of measuring a tissue element, comprising:

irradiating a measurement region with incident light having at least one predetermined wavelength, wherein each beam of the incident light is incident on an incident position to form at least one beam of exit light exited from at least one exit position on the measurement region; and arranging an anti-jitter portion at a position corresponding to the measurement region, so that an average optical path of exit light received by a measurement probe associated with the anti-jitter portion is maintained within a predetermined optical path range during a skin jitter process at the measurement region, a measurement pressure received by the measurement region is determined according to a limit measurement accuracy, and the limit measurement accuracy is a change in the concentration of the measured tissue element when a light energy variation caused by the change in the concentration of the measured tissue element is equal to a target noise level;

wherein the method further comprises:

after arranging the anti-jitter portion at the position corresponding to the measurement region, obtaining an output light intensity corresponding to each beam of the exit light acquired by the measurement probe; and determining a concentration of a measured tissue element according to at least one output light intensity corresponding to the at least one predetermined wavelength;

the anti-jitter portion causes a movement amplitude of a skin at the measurement region to be less than or equal to a movement amplitude threshold; or a mass of the anti-jitter portion is less than or equal to a mass threshold, so that the movement pattern of the anti-jitter portion is consistent with the skin jitter pattern at the measurement region.

* * * * *